(12) United States Patent
Tanabe et al.

(10) Patent No.: US 8,183,044 B2
(45) Date of Patent: May 22, 2012

(54) RECOMBINANT HUMAN HEPATITIS C VIRUS-LIKE PARTICLE AND METHOD FOR PRODUCING THE SAME

(75) Inventors: Jun-ichi Tanabe, Kanagawa (JP); Saburo Sone, Kanagawa (JP); Takaji Wakita, Tokyo (JP); Koji Ishii, Tokyo (JP); Ryosuke Suzuki, Chiba (JP); Tetsuro Suzuki, Tokyo (JP); Tatsuo Miyamura, Tokyo (JP)

(73) Assignees: Japan as represented by Director-General of National Institute of Infectious Diseases, Tokyo (JP); Tokyo Metropolitan Institute of Medical Science, Tokyo (JP); Toray Industries, Inc., Tokyo (JP)

( * ) Notice: Subject to any disclaimer, the term of this patent is extended or adjusted under 35 U.S.C. 154(b) by 403 days.

(21) Appl. No.: 11/992,646

(22) PCT Filed: Sep. 29, 2006

(86) PCT No.: PCT/JP2006/319573
§ 371 (c)(1),
(2), (4) Date: Mar. 27, 2008

(87) PCT Pub. No.: WO2007/037429
PCT Pub. Date: Apr. 5, 2007

(65) Prior Publication Data
US 2009/0221028 A1 Sep. 3, 2009

(30) Foreign Application Priority Data
Sep. 30, 2005 (JP) .................................. 2005-287825

(51) Int. Cl.
*C12N 15/63* (2006.01)
(52) U.S. Cl. .......................... 435/455; 424/218.1; 435/5
(58) Field of Classification Search ........................ None
See application file for complete search history.

(56) References Cited

U.S. PATENT DOCUMENTS
7,659,103 B2 * 2/2010 Wakita et al. .............. 435/235.1
7,674,612 B2 * 3/2010 Rice et al. .................. 435/235.1

FOREIGN PATENT DOCUMENTS
| EP | 1721985 A1 | 11/2006 |
| WO | WO-2004/024904 A2 | 3/2004 |
| WO | WO 2004/044182 A2 * | 5/2004 |
| WO | WO 2005/080575 A1 * | 9/2005 |
| WO | WO-2005/080575 A1 | 9/2005 |

OTHER PUBLICATIONS

Wakita et al. (Jul. 2005, Nature Medicine, vol. 11, p. 791-796).*
Lindenbach et al. (Science, Jul. 2005, vol. 309, p. 623-626).*
Mizushima et al. (Nucleic Acid Research, 1990, vol. 18, p. 5322.*
Neumann et al. (PNAS 1999, vol. 96, p. 9345-9350).*
Date et al. (Journal of Biological Chemistry, 2004, vol. 279, p. 22371-22376).*
Blight (Journal of Virology, 2002, p. 13001-13014).*
Lindenbach et al., "Complete Replication of Hepatitis C Virus in Cell Culture," Science, vol. 309, No. 5734, 2005, pp. 623-626.
Dubensky et al., "Sindbis Virus DNA-Based Expression Vectors: Utility for In Vitro and In Vivo Gene Transfer," Journal of Virology, vol. 70, No. 1, 1996, pp. 508-519.
Emmanuelle Blanchard et al., "Hepatitis C Virus-Like Particle Morphohenesis", Journal of Virology, Apr. 2002, vol. 76, No. 8, pp. 4073-4079, American Society for Microbiology, XP-002512089.
Koji Ishii et al., "Trans-encapsidation of hepatitis C virus subgenomic replicon RNA with viral structure proteins", Biochemical and Biophysical Research Communications, vol. 371, No. 3, Jul. 4, 2008, pp. 446-450, Elsevier Inc.
Pietschmann et al., "Persistent and Transient Replication of Full-Length Hepatitis C Virus Genomes in Cell Culture", Journal of Virology, vol. 76, No. 8, Apr. 2002, pp. 4008-4021.
Pietschmann, T. et al., "Construction and Characterization of Infectious Intragenotypic and Intergenotypic Hepatitis C Virus Chimeras", PNAS, May 2006, vol. 103, No. 19, pp. 7408-7413.

* cited by examiner

*Primary Examiner* — Agniezska Boesen
(74) *Attorney, Agent, or Firm* — Birch, Stewart, Kolasch & Birch, LLP

(57) ABSTRACT

The present invention relates to a method for producing a recombinant hepatitis C virus-like particle comprising the steps of introducing into (i) a cell in which an RNA replicon comprising a nucleotide sequence comprising the 5' untranslated region, the nucleotide sequence coding for the NS3, NS4A, NS4B, NS5A, and NS5B proteins, and the 3' untranslated region of a genome RNA derived from a hepatitis C virus strain autonomously replicates, (ii) a vector expressing the Core, E1, E2, and p7 proteins derived from a hepatitis C virus strain that is the same as or different from that as defined in the above (i), culturing the cell, and recovering the produced virus-like particle, and a recombinant hepatitis C virus particle produced by this method.

10 Claims, 6 Drawing Sheets

SEQUENCE LISTING

```
<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Synthetic primer

<400> SEQUENCE: 1
aaagatctgc gaaaggcctt gtggtactgc                                      30
```

<210> SEQ ID NO 2
<211> LENGTH: 35
<212> TYPE: DNA
<213> ORGANISM: Artificial Sequence
<220> FEATURE:
<223> OTHER INFORMATION: Synthetic primer

<400> SEQUENCE: 2
aagagctctc ataacccgac aagaacaacg ccgcc                        35

<210> SEQ ID NO 3
<211> LENGTH: 35
<212> TYPE: DNA
<213> ORGANISM: Artificial Sequence
<220> FEATURE:
<223> OTHER INFORMATION: Synthetic primer

<400> SEQUENCE: 3
aagagctctc atagacctac aaaaaccccg cctcc                        35

<210> SEQ ID NO 4
<211> LENGTH: 60
<212> TYPE: DNA
<213> ORGANISM: Artificial Sequence
<220> FEATURE:
<223> OTHER INFORMATION: Synthetic primer

<400> SEQUENCE: 4
gtagctgcta ctggtattct tcacctgggc agcggaagct gggatggtca aacaggacag    60

<210> SEQ ID NO 5
<211> LENGTH: 60
<212> TYPE: DNA
<213> ORGANISM: Artificial Sequence
<220> FEATURE:
<223> OTHER INFORMATION: Synthetic primer

<400> SEQUENCE: 5
ctgtcctgtt tgaccatccc agcttccgct gcccaggtga agaataccag tagcagctac    60

<210> SEQ ID NO 6
<211> LENGTH: 35
<212> TYPE: DNA
<213> ORGANISM: Artificial Sequence
<220> FEATURE:
<223> OTHER INFORMATION: Synthetic primer

<400> SEQUENCE: 6
aagagctctc aatcaatatc aacaaaccca cgcct                        35

<210> SEQ ID NO 7
<211> LENGTH: 30
<212> TYPE: DNA
<213> ORGANISM: Artificial Sequence
<220> FEATURE:
<223> OTHER INFORMATION: Synthetic primer

<400> SEQUENCE: 7
aaagatctgc gaaaggcctt gtggtactgc                              30

<210> SEQ ID NO 8
<211> LENGTH: 59
<212> TYPE: DNA
<213> ORGANISM: Artificial Sequence
<220> FEATURE:
<223> OTHER INFORMATION: Synthetic primer

```
<400> SEQUENCE: 8
ggtatatccc ggacacgttg cgcacttcat aagcagagac cggaacggtg atgcaggac      59

<210> SEQ ID NO 9
<211> LENGTH: 59
<212> TYPE: DNA
<213> ORGANISM: Artificial Sequence
<220> FEATURE:
<223> OTHER INFORMATION: Synthetic primer

<400> SEQUENCE: 9
gtcctgcatc accgttccgg tctctgctta tgaagtgcgc aacgtgtccg ggatatacc      59

<210> SEQ ID NO 10
<211> LENGTH: 9678
<212> TYPE: DNA
<213> ORGANISM: Hepatitis C virus
<220> FEATURE:
<221> NAME/KEY: CDS
<222> LOCATION: (341)..(9442)

<400> SEQUENCE: 10
acctgcccct aatagggggcg acactccgcc atgaatcact cccctgtgag gaactactgt    60
cttcacgcag aaagcgccta gccatggcgt tagtatgagt gtcgtacagc ctccaggccc   120 cccccctcccg ggagagccat agtggtctgc ggaaccggtg agtacaccgg aattgccggg   180
aagactgggt cctttcttgg ataaacccac tctatgcccg ccatttggg cgtgcccccg     240 caagactgct agccgagtag cgttgggttg cgaaaggcct tgtggtactg cctgataggg   300
cgcttgcgag tgccccggga ggtctcgtag accgtgcacc atg agc aca aat cct     355
                                              Met Ser Thr Asn Pro
                                              1               5 aaa cct caa aga aaa acc aaa aga aac acc aac cgt cgc cca gaa gac     403
Lys Pro Gln Arg Lys Thr Lys Arg Asn Thr Asn Arg Arg Pro Glu Asp
            10                  15                  20 gtt aag ttc ccg ggc ggc ggt cag atc gtt ggc gga gta tac ttg ttg     451
Val Lys Phe Pro Gly Gly Gly Gln Ile Val Gly Gly Val Tyr Leu Leu
        25                  30                  35 ccg cgc agg ggc ccc agg ttg ggt gtg cgc acg aca agg aaa act tcg     499
Pro Arg Arg Gly Pro Arg Leu Gly Val Arg Thr Thr Arg Lys Thr Ser
    40                  45                  50 gag cgg tcc cag cca cgt ggg aga cgc cag ccc atc ccc aaa gat cgg     547
Glu Arg Ser Gln Pro Arg Gly Arg Arg Gln Pro Ile Pro Lys Asp Arg
55                  60                  65 cgc tcc act ggc aag gcc tgg gga aaa cca ggt cgc ccc tgg ccc cta     595
Arg Ser Thr Gly Lys Ala Trp Gly Lys Pro Gly Arg Pro Trp Pro Leu
70                  75                  80                  85 tat ggg aat gag gga ctc ggc tgg gca gga tgg ctc ctg tcc ccc cga     643
Tyr Gly Asn Glu Gly Leu Gly Trp Ala Gly Trp Leu Leu Ser Pro Arg
                90                  95                 100 ggc tct cgc ccc tcc tgg ggc ccc act gac ccc cgg cat agg tcg cgc     691
Gly Ser Arg Pro Ser Trp Gly Pro Thr Asp Pro Arg His Arg Ser Arg
            105                 110                 115 aac gtg ggt aaa gtc atc gac acc cta acg tgt ggc ttt gcc gac ctc     739
Asn Val Gly Lys Val Ile Asp Thr Leu Thr Cys Gly Phe Ala Asp Leu
        120                 125                 130 atg ggg tac atc ccc gtc gta ggc gcc ccg ctt agt ggc gcc gcc aga     787
Met Gly Tyr Ile Pro Val Val Gly Ala Pro Leu Ser Gly Ala Ala Arg
    135                 140                 145 gct gtc gcg cac ggc gtg aga gtc ctg gag gac ggg gtt aat tat gca     835
Ala Val Ala His Gly Val Arg Val Leu Glu Asp Gly Val Asn Tyr Ala
```

-continued

```
              150                 155                 160                 165
aca ggg aac cta ccc ggt ttc ccc ttt tct atc ttc ttg ctg gcc ctg         883
Thr Gly Asn Leu Pro Gly Phe Pro Phe Ser Ile Phe Leu Leu Ala Leu
                170                 175                 180 ttg tcc tgc atc acc gtt ccg gtc tct gct gcc cag gtg aag aat acc         931
Leu Ser Cys Ile Thr Val Pro Val Ser Ala Ala Gln Val Lys Asn Thr
            185                 190                 195 agt agc agc tac atg gtg acc aat gac tgc tcc aat gac agc atc act         979
Ser Ser Ser Tyr Met Val Thr Asn Asp Cys Ser Asn Asp Ser Ile Thr
        200                 205                 210 tgg cag ctc gag gct gcg gtt ctc cac gtc ccc ggg tgc gtc ccg tgc        1027
Trp Gln Leu Glu Ala Ala Val Leu His Val Pro Gly Cys Val Pro Cys
    215                 220                 225 gag aga gtg ggg aat acg tca cgg tgt tgg gtg cca gtc tcg cca aac        1075
Glu Arg Val Gly Asn Thr Ser Arg Cys Trp Val Pro Val Ser Pro Asn
230                 235                 240                 245 atg gct gtg cgg cag ccc ggt gcc ctc acg cag ggt ctg cgg acg cac        1123
Met Ala Val Arg Gln Pro Gly Ala Leu Thr Gln Gly Leu Arg Thr His
                250                 255                 260 atc gat atg gtt gtg atg tcc gcc acc ttc tgc tct gct ctc tac gtg        1171
Ile Asp Met Val Val Met Ser Ala Thr Phe Cys Ser Ala Leu Tyr Val
            265                 270                 275 ggg gac ctc tgt ggc ggg gtg atg ctc gcg gcc cag gtg ttc atc gtc        1219
Gly Asp Leu Cys Gly Gly Val Met Leu Ala Ala Gln Val Phe Ile Val
        280                 285                 290 tcg ccg cag tac cac tgg ttt gtg caa gaa tgc aat tgc tcc atc tac        1267
Ser Pro Gln Tyr His Trp Phe Val Gln Glu Cys Asn Cys Ser Ile Tyr
    295                 300                 305 cct ggc acc atc act gga cac cgc atg gca tgg gac atg atg atg aac        1315
Pro Gly Thr Ile Thr Gly His Arg Met Ala Trp Asp Met Met Met Asn
310                 315                 320                 325 tgg tcg ccc acg gcc acc atg atc ctg gcg tac gtg atg cgc gtc ccc        1363
Trp Ser Pro Thr Ala Thr Met Ile Leu Ala Tyr Val Met Arg Val Pro
                330                 335                 340 gag gtc atc ata gac atc gtt agc ggg gct cac tgg ggc gtc atg ttc        1411
Glu Val Ile Ile Asp Ile Val Ser Gly Ala His Trp Gly Val Met Phe
            345                 350                 355 ggc ttg gcc tac ttc tct atg cag gga gcg tgg gcg aag gtc att gtc        1459
Gly Leu Ala Tyr Phe Ser Met Gln Gly Ala Trp Ala Lys Val Ile Val
        360                 365                 370 atc ctt ctg ctg gcc gct ggg gtg gac gcg ggc acc acc acc gtt gga        1507
Ile Leu Leu Leu Ala Ala Gly Val Asp Ala Gly Thr Thr Thr Val Gly
    375                 380                 385 ggc gct gtt gca cgt tcc acc aac gtg att gcc ggc gtg ttc agc cat        1555
Gly Ala Val Ala Arg Ser Thr Asn Val Ile Ala Gly Val Phe Ser His
390                 395                 400                 405 ggc cct cag cag aac att cag ctc att aac acc aac ggc agt tgg cac        1603
Gly Pro Gln Gln Asn Ile Gln Leu Ile Asn Thr Asn Gly Ser Trp His
                410                 415                 420 atc aac cgt act gcc ttg aat tgc aat gac tcc ttg aac acc ggc ttt        1651
Ile Asn Arg Thr Ala Leu Asn Cys Asn Asp Ser Leu Asn Thr Gly Phe
            425                 430                 435 ctc gcg gcc ttg ttc tac acc aac cgc ttt aac tcg tca ggg tgt cca        1699
Leu Ala Ala Leu Phe Tyr Thr Asn Arg Phe Asn Ser Ser Gly Cys Pro
        440                 445                 450 ggg cgc ctg tcc gcc tgc cgc aac atc gag gct ttc cgg ata ggg tgg        1747
Gly Arg Leu Ser Ala Cys Arg Asn Ile Glu Ala Phe Arg Ile Gly Trp
    455                 460                 465 ggc acc cta cag tac gag gat aat gtc acc aat cca gag gat atg agg        1795
Gly Thr Leu Gln Tyr Glu Asp Asn Val Thr Asn Pro Glu Asp Met Arg
```

```
              470                 475                 480                 485
ccg tac tgc tgg cac tac ccc cca aag ccg tgt ggc gta gtc ccc gcg         1843
Pro Tyr Cys Trp His Tyr Pro Pro Lys Pro Cys Gly Val Val Pro Ala
                    490                 495                 500 agg tct gtg tgt ggc cca gtg tac tgt ttc acc ccc agc ccg gta gta         1891
Arg Ser Val Cys Gly Pro Val Tyr Cys Phe Thr Pro Ser Pro Val Val
            505                 510                 515 gtg ggc acg acc gac aga cgt gga gtg ccc acc tac aca tgg gga gag         1939
Val Gly Thr Thr Asp Arg Arg Gly Val Pro Thr Tyr Thr Trp Gly Glu
        520                 525                 530 aat gag aca gat gtc ttc cta ctg aac agc acc cga ccg cag ggc             1987
Asn Glu Thr Asp Val Phe Leu Leu Asn Ser Thr Arg Pro Pro Gln Gly
    535                 540                 545 tca tgg ttc ggc tgc acg tgg atg aac tcc act ggt ttc acc aag act         2035
Ser Trp Phe Gly Cys Thr Trp Met Asn Ser Thr Gly Phe Thr Lys Thr
550                 555                 560                 565 tgt ggc gcg cca cct tgc cgc acc aga gct gac ttc aac gcc agc acg         2083
Cys Gly Ala Pro Pro Cys Arg Thr Arg Ala Asp Phe Asn Ala Ser Thr
                570                 575                 580 gac ttg ttg tgc cct acg gat tgt ttt agg aag cat cct gat gcc act         2131
Asp Leu Leu Cys Pro Thr Asp Cys Phe Arg Lys His Pro Asp Ala Thr
            585                 590                 595 tat att aag tgt ggt tct ggg ccc tgg ctc aca cca aag tgc ctg gtc         2179
Tyr Ile Lys Cys Gly Ser Gly Pro Trp Leu Thr Pro Lys Cys Leu Val
        600                 605                 610 cac tac cct tac aga ctc tgg cat tac ccc tgc aca gtc aat ttt acc         2227
His Tyr Pro Tyr Arg Leu Trp His Tyr Pro Cys Thr Val Asn Phe Thr
    615                 620                 625 atc ttc aag ata aga atg tat gta ggg ggg gtt gag cac agg ctc acg         2275
Ile Phe Lys Ile Arg Met Tyr Val Gly Gly Val Glu His Arg Leu Thr
630                 635                 640                 645 gcc gca tgc aac ttc act cgt ggg gat cgc tgc gac ttg gag gac agg         2323
Ala Ala Cys Asn Phe Thr Arg Gly Asp Arg Cys Asp Leu Glu Asp Arg
                650                 655                 660 gac agg agt cag ctg tct cct ctg ttg cac tct acc acg gaa tgg gcc         2371
Asp Arg Ser Gln Leu Ser Pro Leu Leu His Ser Thr Thr Glu Trp Ala
            665                 670                 675 atc ctg ccc tgc acc tac tca gac tta ccc gct ttg tca act ggt ctt         2419
Ile Leu Pro Cys Thr Tyr Ser Asp Leu Pro Ala Leu Ser Thr Gly Leu
        680                 685                 690 ctc cac ctt cac cag aac atc gtg gac gta caa tac atg tat ggc ctc         2467
Leu His Leu His Gln Asn Ile Val Asp Val Gln Tyr Met Tyr Gly Leu
    695                 700                 705 tca cct gct atc aca aaa tac gtc gtt cga tgg gag tgg gtg gta ctc         2515
Ser Pro Ala Ile Thr Lys Tyr Val Val Arg Trp Glu Trp Val Val Leu
710                 715                 720                 725 tta ttc ctg ctc tta gcg gac gcc aga gtc tgc gcc tgc ttg tgg atg         2563
Leu Phe Leu Leu Leu Ala Asp Ala Arg Val Cys Ala Cys Leu Trp Met
                730                 735                 740 ctc atc ttg ttg ggc cag gcc gaa gca gca ttg gag aag ttg gtc gtc         2611
Leu Ile Leu Leu Gly Gln Ala Glu Ala Ala Leu Glu Lys Leu Val Val
            745                 750                 755 ttg cac gct gcg agt gcg gct aac tgc cat ggc ctc cta tat ttt gcc         2659
Leu His Ala Ala Ser Ala Ala Asn Cys His Gly Leu Leu Tyr Phe Ala
        760                 765                 770 atc ttc ttc gtg gca gct tgg cac atc agg ggt cgg gtg gtc ccc ttg         2707
Ile Phe Phe Val Ala Ala Trp His Ile Arg Gly Arg Val Val Pro Leu
    775                 780                 785 acc acc tat tgc ctc act ggc cta tgg ccc ttc tgc cta ctg ctc atg         2755
Thr Thr Tyr Cys Leu Thr Gly Leu Trp Pro Phe Cys Leu Leu Leu Met
```

```
                                                    -continued
      790                 795                 800                 805 gca ctg ccc cgg cag gct tat gcc tat gac gca cct gtg cac gga cag          2803
Ala Leu Pro Arg Gln Ala Tyr Ala Tyr Asp Ala Pro Val His Gly Gln
                    810                 815                 820 ata ggc gtg ggt ttg ttg ata ttg atc acc ctc ttc aca ctc acc ccg          2851
Ile Gly Val Gly Leu Leu Ile Leu Ile Thr Leu Phe Thr Leu Thr Pro
                825                 830                 835 ggg tat aag acc ctc ctc ggc cag tgt ctg tgg tgg ttg tgc tat ctc          2899
Gly Tyr Lys Thr Leu Leu Gly Gln Cys Leu Trp Trp Leu Cys Tyr Leu
            840                 845                 850 ctg acc ctg ggg gaa gcc atg att cag gag tgg gta cca ccc atg cag          2947
Leu Thr Leu Gly Glu Ala Met Ile Gln Glu Trp Val Pro Pro Met Gln
        855                 860                 865 gtg cgc ggc ggc cgc gat ggc atc gcg tgg gcc gtc act ata ttc tgc          2995
Val Arg Gly Gly Arg Asp Gly Ile Ala Trp Ala Val Thr Ile Phe Cys
870                 875                 880                 885 ccg ggt gtg gtg ttt gac att acc aaa tgg ctt ttg gcg ttg ctt ggg          3043
Pro Gly Val Val Phe Asp Ile Thr Lys Trp Leu Leu Ala Leu Leu Gly
                    890                 895                 900 cct gct tac ctc tta agg gcc gct ttg aca cat gtg ccg tac ttc gtc          3091
Pro Ala Tyr Leu Leu Arg Ala Ala Leu Thr His Val Pro Tyr Phe Val
                905                 910                 915 aga gct cac gct ctg ata agg gta tgc gct ttg gtg aag cag ctc gcg          3139
Arg Ala His Ala Leu Ile Arg Val Cys Ala Leu Val Lys Gln Leu Ala
            920                 925                 930 ggg ggt agg tat gtt cag gtg gcg cta ttg gcc ctt ggc agg tgg act          3187
Gly Gly Arg Tyr Val Gln Val Ala Leu Leu Ala Leu Gly Arg Trp Thr
        935                 940                 945 ggc acc tac atc tat gac cac ctc aca cct atg tcg gac tgg gcc gct          3235
Gly Thr Tyr Ile Tyr Asp His Leu Thr Pro Met Ser Asp Trp Ala Ala
950                 955                 960                 965 agc ggc ctg cgc gac tta gcg gtc gcc gtg gaa ccc atc atc ttc agt          3283
Ser Gly Leu Arg Asp Leu Ala Val Ala Val Glu Pro Ile Ile Phe Ser
                    970                 975                 980 ccg atg gag aag aag gtc atc gtc tgg gga gcg gag acg gct gca tgt          3331
Pro Met Glu Lys Lys Val Ile Val Trp Gly Ala Glu Thr Ala Ala Cys
                985                 990                 995 ggg gac att cta cat gga ctt ccc gtg tcc gcc cga ctc ggc cag              3376
Gly Asp Ile Leu His Gly Leu Pro Val Ser Ala Arg Leu Gly Gln
            1000                1005                1010 gag atc ctc ctc ggc cca gct gat ggc tac acc tcc aag ggg tgg              3421
Glu Ile Leu Leu Gly Pro Ala Asp Gly Tyr Thr Ser Lys Gly Trp
        1015                1020                1025 aag ctc ctt gct ccc atc act gct tat gcc cag caa aca cga ggc              3466
Lys Leu Leu Ala Pro Ile Thr Ala Tyr Ala Gln Gln Thr Arg Gly
    1030                1035                1040 ctc ctg ggc gcc ata gtg gtg agt atg acg ggg cgt gac agg aca              3511
Leu Leu Gly Ala Ile Val Val Ser Met Thr Gly Arg Asp Arg Thr
1045                1050                1055 gaa cag gcc ggg gaa gtc caa atc ctg tcc aca gtc tct cag tcc              3556
Glu Gln Ala Gly Glu Val Gln Ile Leu Ser Thr Val Ser Gln Ser
            1060                1065                1070 ttc ctc gga aca acc atc tcg ggg gtt ttg tgg act gtt tac cac              3601
Phe Leu Gly Thr Thr Ile Ser Gly Val Leu Trp Thr Val Tyr His
        1075                1080                1085 gga gct ggc aac aag act cta gcc ggc tta cgg ggt ccg gtc acg              3646
Gly Ala Gly Asn Lys Thr Leu Ala Gly Leu Arg Gly Pro Val Thr
    1090                1095                1100 cag atg tac tcg agt gct gag ggg gac ttg gta ggc tgg ccc agc              3691
Gln Met Tyr Ser Ser Ala Glu Gly Asp Leu Val Gly Trp Pro Ser
```

-continued

|  |  |  | 1105 |  |  |  | 1110 |  |  |  | 1115 |  |  |  |  |
|---|---|---|---|---|---|---|---|---|---|---|---|---|---|---|---|
| ccc | cct | ggg | acc | aag | tct | ttg | gag | ccg | tgc | aag | tgt | gga | gcc | gtc | 3736 |
| Pro | Pro | Gly | Thr | Lys | Ser | Leu | Glu | Pro | Cys | Lys | Cys | Gly | Ala | Val |  |
|  |  | 1120 |  |  |  |  | 1125 |  |  |  |  | 1130 |  |  |  |
| gac | cta | tat | ctg | gtc | acg | cgg | aac | gct | gat | gtc | atc | ccg | gct | cgg | 3781 |
| Asp | Leu | Tyr | Leu | Val | Thr | Arg | Asn | Ala | Asp | Val | Ile | Pro | Ala | Arg |  |
|  | 1135 |  |  |  |  | 1140 |  |  |  |  | 1145 |  |  |  |  |
| aga | cgc | ggg | gac | aag | cgg | gga | gca | ttg | ctc | tcc | ccg | aga | ccc | att | 3826 |
| Arg | Arg | Gly | Asp | Lys | Arg | Gly | Ala | Leu | Leu | Ser | Pro | Arg | Pro | Ile |  |
| 1150 |  |  |  |  | 1155 |  |  |  |  | 1160 |  |  |  |  |  |
| tcg | acc | ttg | aag | ggg | tcc | tcg | ggg | ggg | ccg | gtc | ctc | tgc | cct | agg | 3871 |
| Ser | Thr | Leu | Lys | Gly | Ser | Ser | Gly | Gly | Pro | Val | Leu | Cys | Pro | Arg |  |
|  |  | 1165 |  |  |  |  | 1170 |  |  |  |  | 1175 |  |  |  |
| ggc | cac | gtc | gtt | ggg | ctc | ttc | cga | gca | gct | gtg | tgc | tct | cgg | ggc | 3916 |
| Gly | His | Val | Val | Gly | Leu | Phe | Arg | Ala | Ala | Val | Cys | Ser | Arg | Gly |  |
|  | 1180 |  |  |  |  | 1185 |  |  |  |  | 1190 |  |  |  |  |
| gtg | gcc | aaa | tcc | atc | gat | ttc | atc | ccc | gtt | gag | aca | ctc | gac | gtt | 3961 |
| Val | Ala | Lys | Ser | Ile | Asp | Phe | Ile | Pro | Val | Glu | Thr | Leu | Asp | Val |  |
|  | 1195 |  |  |  |  | 1200 |  |  |  |  | 1205 |  |  |  |  |
| gtt | aca | agg | tct | ccc | act | ttc | agt | gac | aac | agc | acg | cca | ccg | gct | 4006 |
| Val | Thr | Arg | Ser | Pro | Thr | Phe | Ser | Asp | Asn | Ser | Thr | Pro | Pro | Ala |  |
|  | 1210 |  |  |  |  | 1215 |  |  |  |  | 1220 |  |  |  |  |
| gtg | ccc | cag | acc | tat | cag | gtc | ggg | tac | ttg | cat | gct | cca | act | ggc | 4051 |
| Val | Pro | Gln | Thr | Tyr | Gln | Val | Gly | Tyr | Leu | His | Ala | Pro | Thr | Gly |  |
|  | 1225 |  |  |  |  | 1230 |  |  |  |  | 1235 |  |  |  |  |
| agt | gga | aag | agc | acc | aag | gtc | cct | gtc | gcg | tat | gcc | gcc | cag | ggg | 4096 |
| Ser | Gly | Lys | Ser | Thr | Lys | Val | Pro | Val | Ala | Tyr | Ala | Ala | Gln | Gly |  |
|  | 1240 |  |  |  |  | 1245 |  |  |  |  | 1250 |  |  |  |  |
| tac | aaa | gta | cta | gtg | ctt | aac | ccc | tcg | gta | gct | gcc | acc | ctg | ggg | 4141 |
| Tyr | Lys | Val | Leu | Val | Leu | Asn | Pro | Ser | Val | Ala | Ala | Thr | Leu | Gly |  |
|  | 1255 |  |  |  |  | 1260 |  |  |  |  | 1265 |  |  |  |  |
| ttt | ggg | gcg | tac | cta | tcc | aag | gca | cat | ggc | atc | aat | ccc | aac | att | 4186 |
| Phe | Gly | Ala | Tyr | Leu | Ser | Lys | Ala | His | Gly | Ile | Asn | Pro | Asn | Ile |  |
|  | 1270 |  |  |  |  | 1275 |  |  |  |  | 1280 |  |  |  |  |
| agg | act | gga | gtc | agg | acc | gtg | atg | acc | ggg | gag | gcc | atc | acg | tac | 4231 |
| Arg | Thr | Gly | Val | Arg | Thr | Val | Met | Thr | Gly | Glu | Ala | Ile | Thr | Tyr |  |
|  | 1285 |  |  |  |  | 1290 |  |  |  |  | 1295 |  |  |  |  |
| tcc | aca | tat | ggc | aaa | ttt | ctc | gcc | gat | ggg | ggc | tgc | gct | agc | ggc | 4276 |
| Ser | Thr | Tyr | Gly | Lys | Phe | Leu | Ala | Asp | Gly | Gly | Cys | Ala | Ser | Gly |  |
|  | 1300 |  |  |  |  | 1305 |  |  |  |  | 1310 |  |  |  |  |
| gcc | tat | gac | atc | atc | ata | tgc | gat | gaa | tgc | cac | gct | gtg | gat | gct | 4321 |
| Ala | Tyr | Asp | Ile | Ile | Ile | Cys | Asp | Glu | Cys | His | Ala | Val | Asp | Ala |  |
|  | 1315 |  |  |  |  | 1320 |  |  |  |  | 1325 |  |  |  |  |
| acc | tcc | att | ctc | ggc | atc | gga | acg | gtc | ctt | gat | caa | gca | gag | aca | 4366 |
| Thr | Ser | Ile | Leu | Gly | Ile | Gly | Thr | Val | Leu | Asp | Gln | Ala | Glu | Thr |  |
|  | 1330 |  |  |  |  | 1335 |  |  |  |  | 1340 |  |  |  |  |
| gcc | ggg | gtc | aga | cta | act | gtg | ctg | gct | acg | gcc | aca | ccc | ccc | ggg | 4411 |
| Ala | Gly | Val | Arg | Leu | Thr | Val | Leu | Ala | Thr | Ala | Thr | Pro | Pro | Gly |  |
|  | 1345 |  |  |  |  | 1350 |  |  |  |  | 1355 |  |  |  |  |
| tca | gtg | aca | acc | ccc | cat | ccc | gat | ata | gaa | gag | gta | ggc | ctc | ggg | 4456 |
| Ser | Val | Thr | Thr | Pro | His | Pro | Asp | Ile | Glu | Glu | Val | Gly | Leu | Gly |  |
|  | 1360 |  |  |  |  | 1365 |  |  |  |  | 1370 |  |  |  |  |
| cgg | gag | ggt | gag | atc | ccc | ttc | tat | ggg | agg | gcg | att | ccc | cta | tcc | 4501 |
| Arg | Glu | Gly | Glu | Ile | Pro | Phe | Tyr | Gly | Arg | Ala | Ile | Pro | Leu | Ser |  |
|  | 1375 |  |  |  |  | 1380 |  |  |  |  | 1385 |  |  |  |  |
| tgc | atc | aag | gga | ggg | aga | cac | ctg | att | ttc | tgc | cac | tca | aag | aaa | 4546 |
| Cys | Ile | Lys | Gly | Gly | Arg | His | Leu | Ile | Phe | Cys | His | Ser | Lys | Lys |  |
|  | 1390 |  |  |  |  | 1395 |  |  |  |  | 1400 |  |  |  |  |
| aag | tgt | gac | gag | ctc | gcg | gcg | gcc | ctt | cgg | ggc | atg | ggc | ttg | aat | 4591 |
| Lys | Cys | Asp | Glu | Leu | Ala | Ala | Ala | Leu | Arg | Gly | Met | Gly | Leu | Asn |  |

-continued

|  |  |  |  |
|---|---|---|---|
| 1405 | 1410 | 1415 | |
| gcc gtg gca tac tat aga ggg ttg gac gtc tcc ata ata cca gct<br>Ala Val Ala Tyr Tyr Arg Gly Leu Asp Val Ser Ile Ile Pro Ala<br>1420                     1425                   1430 | | | 4636 |
| cag gga gat gtg gtg gtc gtc gcc acc gac gcc ctc atg acg ggg<br>Gln Gly Asp Val Val Val Val Ala Thr Asp Ala Leu Met Thr Gly<br>1435                     1440                   1445 | | | 4681 |
| tac act gga gac ttt gac tcc gtc atc gac tgc aat gta gcg gtc<br>Tyr Thr Gly Asp Phe Asp Ser Val Ile Asp Cys Asn Val Ala Val<br>1450                     1455                   1460 | | | 4726 |
| acc caa gct gtc gac ttc agc ctg gac ccc acc ttc act ata acc<br>Thr Gln Ala Val Asp Phe Ser Leu Asp Pro Thr Phe Thr Ile Thr<br>1465                     1470                   1475 | | | 4771 |
| aca cag act gtc cca caa gac gct gtc tca cgc agt cag cgc cgc<br>Thr Gln Thr Val Pro Gln Asp Ala Val Ser Arg Ser Gln Arg Arg<br>1480                     1485                   1490 | | | 4816 |
| ggg cgc aca ggt aga gga aga cag ggc act tat agg tat gtt tcc<br>Gly Arg Thr Gly Arg Gly Arg Gln Gly Thr Tyr Arg Tyr Val Ser<br>1495                     1500                   1505 | | | 4861 |
| act ggt gaa cga gcc tca gga atg ttt gac agt gta gtg ctt tgt<br>Thr Gly Glu Arg Ala Ser Gly Met Phe Asp Ser Val Val Leu Cys<br>1510                     1515                   1520 | | | 4906 |
| gag tgc tac gac gca ggg gct gcg tgg tac gat ctc aca cca gcg<br>Glu Cys Tyr Asp Ala Gly Ala Ala Trp Tyr Asp Leu Thr Pro Ala<br>1525                     1530                   1535 | | | 4951 |
| gag acc acc gtc agg ctt aga gcg tat ttc aac acg ccc ggc cta<br>Glu Thr Thr Val Arg Leu Arg Ala Tyr Phe Asn Thr Pro Gly Leu<br>1540                     1545                   1550 | | | 4996 |
| ccc gtg tgt caa gac cat ctt gaa ttt tgg gag gca gtt ttc acc<br>Pro Val Cys Gln Asp His Leu Glu Phe Trp Glu Ala Val Phe Thr<br>1555                     1560                   1565 | | | 5041 |
| ggc ctc aca cac ata gac gcc cac ttc ctc tcc caa aca aag caa<br>Gly Leu Thr His Ile Asp Ala His Phe Leu Ser Gln Thr Lys Gln<br>1570                     1575                   1580 | | | 5086 |
| gcg ggg gag aac ttc gcg tac cta gta gcc tac caa gct acg gtg<br>Ala Gly Glu Asn Phe Ala Tyr Leu Val Ala Tyr Gln Ala Thr Val<br>1585                     1590                   1595 | | | 5131 |
| tgc gcc aga gcc aag gcc cct ccc ccg tcc tgg gac gcc atg tgg<br>Cys Ala Arg Ala Lys Ala Pro Pro Pro Ser Trp Asp Ala Met Trp<br>1600                     1605                   1610 | | | 5176 |
| aag tgc ctg gcc cga ctc aag cct acg ctt gcg ggc ccc aca cct<br>Lys Cys Leu Ala Arg Leu Lys Pro Thr Leu Ala Gly Pro Thr Pro<br>1615                     1620                   1625 | | | 5221 |
| ctc ctg tac cgt ttg ggc cct att acc aat gag gtc acc ctc aca<br>Leu Leu Tyr Arg Leu Gly Pro Ile Thr Asn Glu Val Thr Leu Thr<br>1630                     1635                   1640 | | | 5266 |
| cac cct ggg acg aag tac atc gcc aca tgc atg caa gct gac ctt<br>His Pro Gly Thr Lys Tyr Ile Ala Thr Cys Met Gln Ala Asp Leu<br>1645                     1650                   1655 | | | 5311 |
| gag gtc atg acc agc acg tgg gtc cta gct gga gga gtc ctg gca<br>Glu Val Met Thr Ser Thr Trp Val Leu Ala Gly Gly Val Leu Ala<br>1660                     1665                   1670 | | | 5356 |
| gcc gtc gcc gca tat tgc ctg gcg act gga tgc gtt tcc atc atc<br>Ala Val Ala Ala Tyr Cys Leu Ala Thr Gly Cys Val Ser Ile Ile<br>1675                     1680                   1685 | | | 5401 |
| ggc cgc ttg cac gtc aac cag cga gtc gtc gtt gcg ccg gat aag<br>Gly Arg Leu His Val Asn Gln Arg Val Val Val Ala Pro Asp Lys<br>1690                     1695                   1700 | | | 5446 |
| gag gtc ctg tat gag gct ttt gat gag atg gag gaa tgc gcc tct<br>Glu Val Leu Tyr Glu Ala Phe Asp Glu Met Glu Glu Cys Ala Ser | | | 5491 |

-continued

|  |  |  |  |  |  |  |  |  |  |  |  |  |  |  |
|---|---|---|---|---|---|---|---|---|---|---|---|---|---|---|
|  |  |  |  | 1705 |  |  |  | 1710 |  |  |  | 1715 |  |  |
| agg | gcg | gct | ctc | atc | gaa | gag | ggg | cag | cgg | ata | gcc | gag | atg | ttg | 5536 |
| Arg | Ala | Ala | Leu | Ile | Glu | Glu | Gly | Gln | Arg | Ile | Ala | Glu | Met | Leu |  |
|  |  | 1720 |  |  |  |  | 1725 |  |  |  |  | 1730 |  |  |  |
| aag | tcc | aag | atc | caa | ggc | ttg | ctg | cag | cag | gcc | tct | aag | cag | gcc | 5581 |
| Lys | Ser | Lys | Ile | Gln | Gly | Leu | Leu | Gln | Gln | Ala | Ser | Lys | Gln | Ala |  |
|  |  | 1735 |  |  |  |  | 1740 |  |  |  |  | 1745 |  |  |  |
| cag | gac | ata | caa | ccc | gct | atg | cag | gct | tca | tgg | ccc | aaa | gtg | gaa | 5626 |
| Gln | Asp | Ile | Gln | Pro | Ala | Met | Gln | Ala | Ser | Trp | Pro | Lys | Val | Glu |  |
|  |  | 1750 |  |  |  |  | 1755 |  |  |  |  | 1760 |  |  |  |
| caa | ttt | tgg | gcc | aga | cac | atg | tgg | aac | ttc | att | agc | ggc | atc | caa | 5671 |
| Gln | Phe | Trp | Ala | Arg | His | Met | Trp | Asn | Phe | Ile | Ser | Gly | Ile | Gln |  |
|  |  | 1765 |  |  |  |  | 1770 |  |  |  |  | 1775 |  |  |  |
| tac | ctc | gca | gga | ttg | tca | aca | ctg | cca | ggg | aac | ccc | gcg | gtg | gct | 5716 |
| Tyr | Leu | Ala | Gly | Leu | Ser | Thr | Leu | Pro | Gly | Asn | Pro | Ala | Val | Ala |  |
|  |  | 1780 |  |  |  |  | 1785 |  |  |  |  | 1790 |  |  |  |
| tcc | atg | atg | gca | ttc | agt | gcc | gcc | ctc | acc | agt | ccg | ttg | tcg | acc | 5761 |
| Ser | Met | Met | Ala | Phe | Ser | Ala | Ala | Leu | Thr | Ser | Pro | Leu | Ser | Thr |  |
|  |  | 1795 |  |  |  |  | 1800 |  |  |  |  | 1805 |  |  |  |
| agt | acc | acc | atc | ctt | ctc | aac | atc | atg | gga | ggc | tgg | tta | gcg | tcc | 5806 |
| Ser | Thr | Thr | Ile | Leu | Leu | Asn | Ile | Met | Gly | Gly | Trp | Leu | Ala | Ser |  |
|  |  | 1810 |  |  |  |  | 1815 |  |  |  |  | 1820 |  |  |  |
| cag | atc | gca | cca | ccc | gcg | ggg | gcc | acc | ggc | ttt | gtc | gtc | agt | ggc | 5851 |
| Gln | Ile | Ala | Pro | Pro | Ala | Gly | Ala | Thr | Gly | Phe | Val | Val | Ser | Gly |  |
|  |  | 1825 |  |  |  |  | 1830 |  |  |  |  | 1835 |  |  |  |
| ctg | gtg | ggg | gct | gcc | gtg | ggc | agc | ata | ggc | ctg | ggt | aag | gtg | ctg | 5896 |
| Leu | Val | Gly | Ala | Ala | Val | Gly | Ser | Ile | Gly | Leu | Gly | Lys | Val | Leu |  |
|  |  | 1840 |  |  |  |  | 1845 |  |  |  |  | 1850 |  |  |  |
| gtg | gac | atc | ctg | gca | gga | tat | ggt | gcg | ggc | att | tcg | ggg | gcc | ctc | 5941 |
| Val | Asp | Ile | Leu | Ala | Gly | Tyr | Gly | Ala | Gly | Ile | Ser | Gly | Ala | Leu |  |
|  |  | 1855 |  |  |  |  | 1860 |  |  |  |  | 1865 |  |  |  |
| gtc | gca | ttc | aag | atc | atg | tct | ggc | gag | aag | ccc | tct | atg | gaa | gat | 5986 |
| Val | Ala | Phe | Lys | Ile | Met | Ser | Gly | Glu | Lys | Pro | Ser | Met | Glu | Asp |  |
|  |  | 1870 |  |  |  |  | 1875 |  |  |  |  | 1880 |  |  |  |
| gtc | atc | aat | cta | ctg | cct | ggg | atc | ctg | tct | ccg | gga | gcc | ctg | gtg | 6031 |
| Val | Ile | Asn | Leu | Leu | Pro | Gly | Ile | Leu | Ser | Pro | Gly | Ala | Leu | Val |  |
|  |  | 1885 |  |  |  |  | 1890 |  |  |  |  | 1895 |  |  |  |
| gtg | ggg | gtc | atc | tgc | gcg | gcc | att | ctg | cgc | cgc | cac | gtg | gga | ccg | 6076 |
| Val | Gly | Val | Ile | Cys | Ala | Ala | Ile | Leu | Arg | Arg | His | Val | Gly | Pro |  |
|  |  | 1900 |  |  |  |  | 1905 |  |  |  |  | 1910 |  |  |  |
| ggg | gag | ggc | gcg | gtc | caa | tgg | atg | aac | agg | ctt | att | gcc | ttt | gct | 6121 |
| Gly | Glu | Gly | Ala | Val | Gln | Trp | Met | Asn | Arg | Leu | Ile | Ala | Phe | Ala |  |
|  |  | 1915 |  |  |  |  | 1920 |  |  |  |  | 1925 |  |  |  |
| tcc | aga | gga | aac | cac | gtc | gcc | cct | act | cac | tac | gtg | acg | gag | tcg | 6166 |
| Ser | Arg | Gly | Asn | His | Val | Ala | Pro | Thr | His | Tyr | Val | Thr | Glu | Ser |  |
|  |  | 1930 |  |  |  |  | 1935 |  |  |  |  | 1940 |  |  |  |
| gat | gcg | tcg | cag | cgt | gtg | acc | caa | cta | ctt | ggc | tct | ctt | act | ata | 6211 |
| Asp | Ala | Ser | Gln | Arg | Val | Thr | Gln | Leu | Leu | Gly | Ser | Leu | Thr | Ile |  |
|  |  | 1945 |  |  |  |  | 1950 |  |  |  |  | 1955 |  |  |  |
| acc | agc | cta | ctc | aga | aga | ctc | cac | aat | tgg | ata | act | gag | gac | tgc | 6256 |
| Thr | Ser | Leu | Leu | Arg | Arg | Leu | His | Asn | Trp | Ile | Thr | Glu | Asp | Cys |  |
|  |  | 1960 |  |  |  |  | 1965 |  |  |  |  | 1970 |  |  |  |
| ccc | atc | cca | tgc | tcc | gga | tcc | tgg | ctc | cgc | gac | gtg | tgg | gac | tgg | 6301 |
| Pro | Ile | Pro | Cys | Ser | Gly | Ser | Trp | Leu | Arg | Asp | Val | Trp | Asp | Trp |  |
|  |  | 1975 |  |  |  |  | 1980 |  |  |  |  | 1985 |  |  |  |
| gtt | tgc | acc | atc | ttg | aca | gac | ttc | aaa | aat | tgg | ctg | acc | tct | aaa | 6346 |
| Val | Cys | Thr | Ile | Leu | Thr | Asp | Phe | Lys | Asn | Trp | Leu | Thr | Ser | Lys |  |
|  |  | 1990 |  |  |  |  | 1995 |  |  |  |  | 2000 |  |  |  |
| ttg | ttc | ccc | aag | ctg | ccc | ggc | ctc | ccc | ttc | atc | tct | tgt | caa | aag | 6391 |
| Leu | Phe | Pro | Lys | Leu | Pro | Gly | Leu | Pro | Phe | Ile | Ser | Cys | Gln | Lys |  |

-continued

|  |  |  |  |  |  |  |  |  |  |  |  |  |  |  |  |
|---|---|---|---|---|---|---|---|---|---|---|---|---|---|---|---|
|  |  | 2005 |  |  |  | 2010 |  |  |  | 2015 |  |  |  |  |  |
| ggg | tac | aag | ggt | gtg | tgg | gcc | ggc | act | ggc | atc | atg | acc | acg | cgc | 6436 |
| Gly | Tyr | Lys | Gly | Val | Trp | Ala | Gly | Thr | Gly | Ile | Met | Thr | Thr | Arg |  |
|  |  | 2020 |  |  |  | 2025 |  |  |  | 2030 |  |  |  |  |  |
| tgc | cct | tgc | ggc | gcc | aac | atc | tct | ggc | aat | gtc | cgc | ctg | ggc | tct | 6481 |
| Cys | Pro | Cys | Gly | Ala | Asn | Ile | Ser | Gly | Asn | Val | Arg | Leu | Gly | Ser |  |
|  |  | 2035 |  |  |  | 2040 |  |  |  | 2045 |  |  |  |  |  |
| atg | agg | atc | aca | ggg | cct | aaa | acc | tgc | atg | aac | acc | tgg | cag | ggg | 6526 |
| Met | Arg | Ile | Thr | Gly | Pro | Lys | Thr | Cys | Met | Asn | Thr | Trp | Gln | Gly |  |
|  |  | 2050 |  |  |  | 2055 |  |  |  | 2060 |  |  |  |  |  |
| acc | ttt | cct | atc | aat | tgc | tac | acg | gag | ggc | cag | tgc | gcg | ccg | aaa | 6571 |
| Thr | Phe | Pro | Ile | Asn | Cys | Tyr | Thr | Glu | Gly | Gln | Cys | Ala | Pro | Lys |  |
|  |  | 2065 |  |  |  | 2070 |  |  |  | 2075 |  |  |  |  |  |
| ccc | ccc | acg | aac | tac | aag | acc | gcc | atc | tgg | agg | gtg | gcg | gcc | tcg | 6616 |
| Pro | Pro | Thr | Asn | Tyr | Lys | Thr | Ala | Ile | Trp | Arg | Val | Ala | Ala | Ser |  |
|  |  | 2080 |  |  |  | 2085 |  |  |  | 2090 |  |  |  |  |  |
| gag | tac | gcg | gag | gtg | acg | cag | cat | ggg | tcg | tac | tcc | tat | gta | aca | 6661 |
| Glu | Tyr | Ala | Glu | Val | Thr | Gln | His | Gly | Ser | Tyr | Ser | Tyr | Val | Thr |  |
|  |  | 2095 |  |  |  | 2100 |  |  |  | 2105 |  |  |  |  |  |
| gga | ctg | acc | act | gac | aat | ctg | aaa | att | cct | tgc | caa | cta | cct | tct | 6706 |
| Gly | Leu | Thr | Thr | Asp | Asn | Leu | Lys | Ile | Pro | Cys | Gln | Leu | Pro | Ser |  |
|  |  | 2110 |  |  |  | 2115 |  |  |  | 2120 |  |  |  |  |  |
| cca | gag | ttt | ttc | tcc | tgg | gtg | gac | ggt | gtg | cag | atc | cat | agg | ttt | 6751 |
| Pro | Glu | Phe | Phe | Ser | Trp | Val | Asp | Gly | Val | Gln | Ile | His | Arg | Phe |  |
|  |  | 2125 |  |  |  | 2130 |  |  |  | 2135 |  |  |  |  |  |
| gca | ccc | aca | cca | aag | ccg | ttt | ttc | cgg | gat | gag | gtc | tcg | ttc | tgc | 6796 |
| Ala | Pro | Thr | Pro | Lys | Pro | Phe | Phe | Arg | Asp | Glu | Val | Ser | Phe | Cys |  |
|  |  | 2140 |  |  |  | 2145 |  |  |  | 2150 |  |  |  |  |  |
| gtt | ggg | ctt | aat | tcc | tat | gct | gtc | ggg | tcc | cag | ctt | ccc | tgt | gaa | 6841 |
| Val | Gly | Leu | Asn | Ser | Tyr | Ala | Val | Gly | Ser | Gln | Leu | Pro | Cys | Glu |  |
|  |  | 2155 |  |  |  | 2160 |  |  |  | 2165 |  |  |  |  |  |
| cct | gag | ccc | gac | gca | gac | gta | ttg | agg | tcc | atg | cta | aca | gat | ccg | 6886 |
| Pro | Glu | Pro | Asp | Ala | Asp | Val | Leu | Arg | Ser | Met | Leu | Thr | Asp | Pro |  |
|  |  | 2170 |  |  |  | 2175 |  |  |  | 2180 |  |  |  |  |  |
| ccc | cac | atc | acg | gcg | gag | act | gcg | gcg | cgg | cgc | ttg | gca | cgg | gga | 6931 |
| Pro | His | Ile | Thr | Ala | Glu | Thr | Ala | Ala | Arg | Arg | Leu | Ala | Arg | Gly |  |
|  |  | 2185 |  |  |  | 2190 |  |  |  | 2195 |  |  |  |  |  |
| tca | cct | cca | tct | gag | gcg | agc | tcc | tca | gtg | agc | cag | cta | tca | gca | 6976 |
| Ser | Pro | Pro | Ser | Glu | Ala | Ser | Ser | Ser | Val | Ser | Gln | Leu | Ser | Ala |  |
|  |  | 2200 |  |  |  | 2205 |  |  |  | 2210 |  |  |  |  |  |
| ccg | tcg | ctg | cgg | gcc | acc | tgc | acc | acc | cac | agc | aac | acc | tat | gac | 7021 |
| Pro | Ser | Leu | Arg | Ala | Thr | Cys | Thr | Thr | His | Ser | Asn | Thr | Tyr | Asp |  |
|  |  | 2215 |  |  |  | 2220 |  |  |  | 2225 |  |  |  |  |  |
| gtg | gac | atg | gtc | gat | gcc | aac | ctg | ctc | atg | gag | ggc | ggt | gtg | gct | 7066 |
| Val | Asp | Met | Val | Asp | Ala | Asn | Leu | Leu | Met | Glu | Gly | Gly | Val | Ala |  |
|  |  | 2230 |  |  |  | 2235 |  |  |  | 2240 |  |  |  |  |  |
| cag | aca | gag | cct | gag | tcc | agg | gtg | ccc | gtt | ctg | gac | ttt | ctc | gag | 7111 |
| Gln | Thr | Glu | Pro | Glu | Ser | Arg | Val | Pro | Val | Leu | Asp | Phe | Leu | Glu |  |
|  |  | 2245 |  |  |  | 2250 |  |  |  | 2255 |  |  |  |  |  |
| cca | atg | gcc | gag | gaa | gag | agc | gac | ctt | gag | ccc | tca | ata | cca | tcg | 7156 |
| Pro | Met | Ala | Glu | Glu | Glu | Ser | Asp | Leu | Glu | Pro | Ser | Ile | Pro | Ser |  |
|  |  | 2260 |  |  |  | 2265 |  |  |  | 2270 |  |  |  |  |  |
| gag | tgc | atg | ctc | ccc | agg | agc | ggg | ttt | cca | cgg | gcc | tta | ccg | gct | 7201 |
| Glu | Cys | Met | Leu | Pro | Arg | Ser | Gly | Phe | Pro | Arg | Ala | Leu | Pro | Ala |  |
|  |  | 2275 |  |  |  | 2280 |  |  |  | 2285 |  |  |  |  |  |
| tgg | gca | cgg | cct | gac | tac | aac | ccg | ccg | ctc | gtg | gaa | tcg | tgg | agg | 7246 |
| Trp | Ala | Arg | Pro | Asp | Tyr | Asn | Pro | Pro | Leu | Val | Glu | Ser | Trp | Arg |  |
|  |  | 2290 |  |  |  | 2295 |  |  |  | 2300 |  |  |  |  |  |
| agg | cca | gat | tac | caa | ccg | ccc | acc | gtt | gct | ggt | tgt | gct | ctc | ccc | 7291 |
| Arg | Pro | Asp | Tyr | Gln | Pro | Pro | Thr | Val | Ala | Gly | Cys | Ala | Leu | Pro |  |

|     |     |     |     |     |     |     |     |     |     |     |     |      |
| --- | --- | --- | --- | --- | --- | --- | --- | --- | --- | --- | --- | ---- |
|     |     | 2305 |    |     |     | 2310 |    |     |     | 2315 |    |      |
| ccc | ccc | aag | aag | gcc | ccg | acg | cct | ccc | cca | agg | aga | cgc | cgg | aca | 7336 |
| Pro | Pro | Lys | Lys | Ala | Pro | Thr | Pro | Pro | Pro | Arg | Arg | Arg | Arg | Thr |      |
|     |     | 2320 |    |     |     | 2325 |    |     |     | 2330 |    |      |
| gtg | ggt | ctg | agc | gag | agc | acc | ata | tca | gaa | gcc | ctc | cag | caa | ctg | 7381 |
| Val | Gly | Leu | Ser | Glu | Ser | Thr | Ile | Ser | Glu | Ala | Leu | Gln | Gln | Leu |      |
|     |     | 2335 |    |     |     | 2340 |    |     |     | 2345 |    |      |
| gcc | atc | aag | acc | ttt | ggc | cag | ccc | ccc | tcg | agc | ggt | gat | gca | ggc | 7426 |
| Ala | Ile | Lys | Thr | Phe | Gly | Gln | Pro | Pro | Ser | Ser | Gly | Asp | Ala | Gly |      |
|     |     | 2350 |    |     |     | 2355 |    |     |     | 2360 |    |      |
| tcg | tcc | acg | ggg | gcg | ggc | gcc | gcc | gaa | tcc | ggc | ggt | ccg | acg | tcc | 7471 |
| Ser | Ser | Thr | Gly | Ala | Gly | Ala | Ala | Glu | Ser | Gly | Gly | Pro | Thr | Ser |      |
|     |     | 2365 |    |     |     | 2370 |    |     |     | 2375 |    |      |
| cct | ggt | gag | ccg | gcc | ccc | tca | gag | aca | ggt | tcc | gcc | tcc | tct | atg | 7516 |
| Pro | Gly | Glu | Pro | Ala | Pro | Ser | Glu | Thr | Gly | Ser | Ala | Ser | Ser | Met |      |
|     |     | 2380 |    |     |     | 2385 |    |     |     | 2390 |    |      |
| ccc | ccc | ctc | gag | ggg | gag | cct | gga | gat | ccg | gac | ctg | gag | tct | gat | 7561 |
| Pro | Pro | Leu | Glu | Gly | Glu | Pro | Gly | Asp | Pro | Asp | Leu | Glu | Ser | Asp |      |
|     |     | 2395 |    |     |     | 2400 |    |     |     | 2405 |    |      |
| cag | gta | gag | ctt | caa | cct | ccc | ccc | cag | ggg | ggg | ggg | gta | gct | ccc | 7606 |
| Gln | Val | Glu | Leu | Gln | Pro | Pro | Pro | Gln | Gly | Gly | Gly | Val | Ala | Pro |      |
|     |     | 2410 |    |     |     | 2415 |    |     |     | 2420 |    |      |
| ggt | tcg | ggc | tcg | ggg | tct | tgg | tct | act | tgc | tcc | gag | gag | gac | gat | 7651 |
| Gly | Ser | Gly | Ser | Gly | Ser | Trp | Ser | Thr | Cys | Ser | Glu | Glu | Asp | Asp |      |
|     |     | 2425 |    |     |     | 2430 |    |     |     | 2435 |    |      |
| acc | acc | gtg | tgc | tgc | tcc | atg | tca | tac | tcc | tgg | acc | ggg | gct | cta | 7696 |
| Thr | Thr | Val | Cys | Cys | Ser | Met | Ser | Tyr | Ser | Trp | Thr | Gly | Ala | Leu |      |
|     |     | 2440 |    |     |     | 2445 |    |     |     | 2450 |    |      |
| ata | act | ccc | tgt | agc | ccc | gaa | gag | gaa | aag | ttg | cca | atc | aac | cct | 7741 |
| Ile | Thr | Pro | Cys | Ser | Pro | Glu | Glu | Glu | Lys | Leu | Pro | Ile | Asn | Pro |      |
|     |     | 2455 |    |     |     | 2460 |    |     |     | 2465 |    |      |
| ttg | agt | aac | tcg | ctg | ttg | cga | tac | cat | aac | aag | gtg | tac | tgt | aca | 7786 |
| Leu | Ser | Asn | Ser | Leu | Leu | Arg | Tyr | His | Asn | Lys | Val | Tyr | Cys | Thr |      |
|     |     | 2470 |    |     |     | 2475 |    |     |     | 2480 |    |      |
| aca | tca | aag | agc | gcc | tca | cag | agg | gct | aaa | aag | gta | act | ttt | gac | 7831 |
| Thr | Ser | Lys | Ser | Ala | Ser | Gln | Arg | Ala | Lys | Lys | Val | Thr | Phe | Asp |      |
|     |     | 2485 |    |     |     | 2490 |    |     |     | 2495 |    |      |
| agg | acg | caa | gtg | ctc | gac | gcc | cat | tat | gac | tca | gtc | tta | aag | gac | 7876 |
| Arg | Thr | Gln | Val | Leu | Asp | Ala | His | Tyr | Asp | Ser | Val | Leu | Lys | Asp |      |
|     |     | 2500 |    |     |     | 2505 |    |     |     | 2510 |    |      |
| atc | aag | cta | gcg | gct | tcc | aag | gtc | agc | gca | agg | ctc | ctc | acc | ttg | 7921 |
| Ile | Lys | Leu | Ala | Ala | Ser | Lys | Val | Ser | Ala | Arg | Leu | Leu | Thr | Leu |      |
|     |     | 2515 |    |     |     | 2520 |    |     |     | 2525 |    |      |
| gag | gag | gcg | tgc | cag | ttg | act | cca | ccc | cat | tct | gca | aga | tcc | aag | 7966 |
| Glu | Glu | Ala | Cys | Gln | Leu | Thr | Pro | Pro | His | Ser | Ala | Arg | Ser | Lys |      |
|     |     | 2530 |    |     |     | 2535 |    |     |     | 2540 |    |      |
| tat | gga | ttc | ggg | gcc | aag | gag | gtc | cgc | agc | ttg | tcc | ggg | agg | gcc | 8011 |
| Tyr | Gly | Phe | Gly | Ala | Lys | Glu | Val | Arg | Ser | Leu | Ser | Gly | Arg | Ala |      |
|     |     | 2545 |    |     |     | 2550 |    |     |     | 2555 |    |      |
| gtt | aac | cac | atc | aag | tcc | gtg | tgg | aag | gac | ctc | ctg | gaa | gac | cca | 8056 |
| Val | Asn | His | Ile | Lys | Ser | Val | Trp | Lys | Asp | Leu | Leu | Glu | Asp | Pro |      |
|     |     | 2560 |    |     |     | 2565 |    |     |     | 2570 |    |      |
| caa | aca | cca | att | ccc | aca | acc | atc | atg | gcc | aaa | aat | gag | gtg | ttc | 8101 |
| Gln | Thr | Pro | Ile | Pro | Thr | Thr | Ile | Met | Ala | Lys | Asn | Glu | Val | Phe |      |
|     |     | 2575 |    |     |     | 2580 |    |     |     | 2585 |    |      |
| tgc | gtg | gac | ccc | gcc | aag | ggg | ggt | aag | aaa | cca | gct | cgc | ctc | atc | 8146 |
| Cys | Val | Asp | Pro | Ala | Lys | Gly | Gly | Lys | Lys | Pro | Ala | Arg | Leu | Ile |      |
|     |     | 2590 |    |     |     | 2595 |    |     |     | 2600 |    |      |
| gtt | tac | cct | gac | ctc | ggc | gtc | cgg | gtc | tgc | gag | aaa | atg | gcc | ctc | 8191 |
| Val | Tyr | Pro | Asp | Leu | Gly | Val | Arg | Val | Cys | Glu | Lys | Met | Ala | Leu |      |

```
                   2605                  2610                   2615
tat gac att aca caa aag ctt cct cag gcg gta atg gga gct tcc          8236
Tyr Asp Ile Thr Gln Lys Leu Pro Gln Ala Val Met Gly Ala Ser
            2620                  2625                  2630 tat ggc ttc cag tac tcc cct gcc caa cgg gtg gag tat ctc ttg          8281
Tyr Gly Phe Gln Tyr Ser Pro Ala Gln Arg Val Glu Tyr Leu Leu
            2635                  2640                  2645 aaa gca tgg gcg gaa aag aag gac ccc atg ggt ttt tcg tat gat          8326
Lys Ala Trp Ala Glu Lys Lys Asp Pro Met Gly Phe Ser Tyr Asp
            2650                  2655                  2660 acc cga tgc ttc gac tca acc gtc act gag aga gac atc agg acc          8371
Thr Arg Cys Phe Asp Ser Thr Val Thr Glu Arg Asp Ile Arg Thr
            2665                  2670                  2675 gag gag tcc ata tac cag gcc tgc tcc ctg ccc gag gag gcc cgc          8416
Glu Glu Ser Ile Tyr Gln Ala Cys Ser Leu Pro Glu Glu Ala Arg
            2680                  2685                  2690 act gcc ata cac tcg ctg act gag aga ctt tac gta gga ggg ccc          8461
Thr Ala Ile His Ser Leu Thr Glu Arg Leu Tyr Val Gly Gly Pro
            2695                  2700                  2705 atg ttc aac agc aag ggt caa acc tgc ggt tac aga cgt tgc cgc          8506
Met Phe Asn Ser Lys Gly Gln Thr Cys Gly Tyr Arg Arg Cys Arg
            2710                  2715                  2720 gcc agc ggg gtg cta acc act agc atg ggt aac acc atc aca tgc          8551
Ala Ser Gly Val Leu Thr Thr Ser Met Gly Asn Thr Ile Thr Cys
            2725                  2730                  2735 tat gtg aaa gcc cta gcg gcc tgc aag gct gcg ggg ata gtt gcg          8596
Tyr Val Lys Ala Leu Ala Ala Cys Lys Ala Ala Gly Ile Val Ala
            2740                  2745                  2750 ccc aca atg ctg gta tgc ggc gat gac cta gta gtc atc tca gaa          8641
Pro Thr Met Leu Val Cys Gly Asp Asp Leu Val Val Ile Ser Glu
            2755                  2760                  2765 agc cag ggg act gag gag gac gag cgg aac ctg aga gcc ttc acg          8686
Ser Gln Gly Thr Glu Glu Asp Glu Arg Asn Leu Arg Ala Phe Thr
            2770                  2775                  2780 gag gcc atg acc agg tac tct gcc cct cct ggt gat ccc ccc aga          8731
Glu Ala Met Thr Arg Tyr Ser Ala Pro Pro Gly Asp Pro Pro Arg
            2785                  2790                  2795 ccg gaa tat gac ctg gag cta ata aca tcc tgt tcc tca aat gtg          8776
Pro Glu Tyr Asp Leu Glu Leu Ile Thr Ser Cys Ser Ser Asn Val
            2800                  2805                  2810 tct gtg gcg ttg ggc ccg cgg ggc cgc cgc aga tac tac ctg acc          8821
Ser Val Ala Leu Gly Pro Arg Gly Arg Arg Arg Tyr Tyr Leu Thr
            2815                  2820                  2825 aga gac cca acc act cca ctc gcc cgg gct gcc tgg gaa aca gtt          8866
Arg Asp Pro Thr Thr Pro Leu Ala Arg Ala Ala Trp Glu Thr Val
            2830                  2835                  2840 aga cac tcc cct atc aat tca tgg ctg gga aac atc atc cag tat          8911
Arg His Ser Pro Ile Asn Ser Trp Leu Gly Asn Ile Ile Gln Tyr
            2845                  2850                  2855 gct cca acc ata tgg gtt cgc atg gtc cta atg aca cac ttc ttc          8956
Ala Pro Thr Ile Trp Val Arg Met Val Leu Met Thr His Phe Phe
            2860                  2865                  2870 tcc att ctc atg gtc caa gac acc ctg gac cag aac ctc aac ttt          9001
Ser Ile Leu Met Val Gln Asp Thr Leu Asp Gln Asn Leu Asn Phe
            2875                  2880                  2885 gag atg tat gga tca gta tac tcc gtg aat cct ttg gac ctt cca          9046
Glu Met Tyr Gly Ser Val Tyr Ser Val Asn Pro Leu Asp Leu Pro
            2890                  2895                  2900 gcc ata att gag agg tta cac ggg ctt gac gcc ttt tct atg cac          9091
Ala Ile Ile Glu Arg Leu His Gly Leu Asp Ala Phe Ser Met His
```

-continued

|     |     |     | 2905 |     |     |     | 2910 |     |     |     | 2915 |     |     |     |      |
|-----|-----|-----|------|-----|-----|-----|------|-----|-----|-----|------|-----|-----|-----|------|
| aca | tac | tct | cac  | cac | gaa | ctg | acg  | cgg | gtg | gct | tca  | gcc | ctc | aga | 9136 |
| Thr | Tyr | Ser | His  | His | Glu | Leu | Thr  | Arg | Val | Ala | Ser  | Ala | Leu | Arg |      |
|     |     |     | 2920 |     |     |     | 2925 |     |     |     | 2930 |     |     |     |      |

| aaa | ctt | ggg | gcg  | cca | ccc | ctc | agg  | gtg | tgg | aag | agt  | cgg | gct | cgc | 9181 |
|-----|-----|-----|------|-----|-----|-----|------|-----|-----|-----|------|-----|-----|-----|------|
| Lys | Leu | Gly | Ala  | Pro | Pro | Leu | Arg  | Val | Trp | Lys | Ser  | Arg | Ala | Arg |      |
|     |     |     | 2935 |     |     |     | 2940 |     |     |     | 2945 |     |     |     |      |

| gca | gtc | agg | gcg  | tcc | ctc | atc | tcc  | cgt | gga | ggg | aaa  | gcg | gcc | gtt | 9226 |
|-----|-----|-----|------|-----|-----|-----|------|-----|-----|-----|------|-----|-----|-----|------|
| Ala | Val | Arg | Ala  | Ser | Leu | Ile | Ser  | Arg | Gly | Gly | Lys  | Ala | Ala | Val |      |
|     |     |     | 2950 |     |     |     | 2955 |     |     |     | 2960 |     |     |     |      |

| tgc | ggc | cga | tat  | ctc | ttc | aat | tgg  | gcg | gtg | aag | acc  | aag | ctc | aaa | 9271 |
|-----|-----|-----|------|-----|-----|-----|------|-----|-----|-----|------|-----|-----|-----|------|
| Cys | Gly | Arg | Tyr  | Leu | Phe | Asn | Trp  | Ala | Val | Lys | Thr  | Lys | Leu | Lys |      |
|     |     |     | 2965 |     |     |     | 2970 |     |     |     | 2975 |     |     |     |      |

| ctc | act | cca | ttg  | ccg | gag | gcg | cgc  | cta | ctg | gac | tta  | tcc | agt | tgg | 9316 |
|-----|-----|-----|------|-----|-----|-----|------|-----|-----|-----|------|-----|-----|-----|------|
| Leu | Thr | Pro | Leu  | Pro | Glu | Ala | Arg  | Leu | Leu | Asp | Leu  | Ser | Ser | Trp |      |
|     |     |     | 2980 |     |     |     | 2985 |     |     |     | 2990 |     |     |     |      |

| ttc | acc | gtc | ggc  | gcc | ggc | ggg | ggc  | gac | att | ttt | cac  | agc | gtg | tcg | 9361 |
|-----|-----|-----|------|-----|-----|-----|------|-----|-----|-----|------|-----|-----|-----|------|
| Phe | Thr | Val | Gly  | Ala | Gly | Gly | Gly  | Asp | Ile | Phe | His  | Ser | Val | Ser |      |
|     |     |     | 2995 |     |     |     | 3000 |     |     |     | 3005 |     |     |     |      |

| cgc | gcc | cga | ccc  | cgc | tca | tta | ctc  | ttc | ggc | cta | ctc  | ctt | ttc |     | 9406 |
|-----|-----|-----|------|-----|-----|-----|------|-----|-----|-----|------|-----|-----|-----|------|
| Arg | Ala | Arg | Pro  | Arg | Ser | Leu | Leu  | Phe | Gly | Leu | Leu  | Leu | Phe |     |      |
|     |     |     | 3010 |     |     |     | 3015 |     |     |     | 3020 |     |     |     |      |

| gta | ggg | gta | ggc  | ctc | ttc | cta | ctc  | ccc | gct | cgg | tag  | agcggcacac |   | 9452 |
|-----|-----|-----|------|-----|-----|-----|------|-----|-----|-----|------|-----|-----|-----|------|
| Val | Gly | Val | Gly  | Leu | Phe | Leu | Leu  | Pro | Ala | Arg |      |     |     |     |      |
|     |     |     | 3025 |     |     |     | 3030 |     |     |     |      |     |     |     |      | actaggtaca ctccatagct aactgttcct tttttttttt tttttttttt tttttttttt    9512 tttttttttt ttcttttttt ttttttttccc tctttcttcc cttctcatct tattctactt    9572 tctttcttgg tggctccatc ttagccctag tcacggctag ctgtgaaagg tccgtgagcc    9632 gcatgactgc agagagtgcc gtaactggtc tctctgcaga tcatgt    9678

<210> SEQ ID NO 11
<211> LENGTH: 3033
<212> TYPE: PRT
<213> ORGANISM: Hepatitis C virus

<400> SEQUENCE: 11

Met Ser Thr Asn Pro Lys Pro Gln Arg Lys Thr Lys Arg Asn Thr Asn
1               5                   10                  15

Arg Arg Pro Glu Asp Val Lys Phe Pro Gly Gly Gly Gln Ile Val Gly
                20                  25                  30

Gly Val Tyr Leu Leu Pro Arg Arg Gly Pro Arg Leu Gly Val Arg Thr
            35                  40                  45

Thr Arg Lys Thr Ser Glu Arg Ser Gln Pro Arg Gly Arg Arg Gln Pro
        50                  55                  60

Ile Pro Lys Asp Arg Arg Ser Thr Gly Lys Ala Trp Gly Lys Pro Gly
65                  70                  75                  80

Arg Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Ser Gly Ala Ala Arg Ala Val Ala His Gly Val Arg Val Leu Glu Asp
145                 150                 155                 160

```
Gly Val Asn Tyr Ala Thr Gly Asn Leu Pro Gly Phe Pro Phe Ser Ile
                165                 170                 175

Phe Leu Leu Ala Leu Leu Ser Cys Ile Thr Val Pro Val Ser Ala Ala
            180                 185                 190

Gln Val Lys Asn Thr Ser Ser Tyr Met Val Thr Asn Asp Cys Ser
        195                 200                 205

Asn Asp Ser Ile Thr Trp Gln Leu Glu Ala Ala Val Leu His Val Pro
    210                 215                 220

Gly Cys Val Pro Cys Glu Arg Val Gly Asn Thr Ser Arg Cys Trp Val
225                 230                 235                 240

Pro Val Ser Pro Asn Met Ala Val Arg Gln Pro Gly Ala Leu Thr Gln
            245                 250                 255

Gly Leu Arg Thr His Ile Asp Met Val Val Met Ser Ala Thr Phe Cys
            260                 265                 270

Ser Ala Leu Tyr Val Gly Asp Leu Cys Gly Val Met Leu Ala Ala
        275                 280                 285

Gln Val Phe Ile Val Ser Pro Gln Tyr His Trp Phe Val Gln Glu Cys
        290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Val Met Arg Val Pro Glu Val Ile Ile Asp Ile Val Ser Gly Ala His
            340                 345                 350

Trp Gly Val Met Phe Gly Leu Ala Tyr Phe Ser Met Gln Gly Ala Trp
            355                 360                 365

Ala Lys Val Ile Val Ile Leu Leu Leu Ala Ala Gly Val Asp Ala Gly
        370                 375                 380

Thr Thr Thr Val Gly Gly Ala Val Ala Arg Ser Thr Asn Val Ile Ala
385                 390                 395                 400

Gly Val Phe Ser His Gly Pro Gln Gln Asn Ile Gln Leu Ile Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Thr Asn Arg Phe Asn
        435                 440                 445

Ser Ser Gly Cys Pro Gly Arg Leu Ser Ala Cys Arg Asn Ile Glu Ala
    450                 455                 460

Phe Arg Ile Gly Trp Gly Thr Leu Gln Tyr Glu Asp Asn Val Thr Asn
465                 470                 475                 480

Pro Glu Asp Met Arg Pro Tyr Cys Trp His Tyr Pro Pro Lys Pro Cys
                485                 490                 495

Gly Val Val Pro Ala Arg Ser Val Cys Gly Pro Val Tyr Cys Phe Thr
            500                 505                 510

Pro Ser Pro Val Val Gly Thr Thr Asp Arg Arg Gly Val Pro Thr
        515                 520                 525

Tyr Thr Trp Gly Glu Asn Glu Thr Asp Val Phe Leu Leu Asn Ser Thr
        530                 535                 540

Arg Pro Pro Gln Gly Ser Trp Phe Gly Cys Thr Trp Met Asn Ser Thr
545                 550                 555                 560

Gly Phe Thr Lys Thr Cys Gly Ala Pro Pro Cys Arg Thr Arg Ala Asp
                565                 570                 575

Phe Asn Ala Ser Thr Asp Leu Leu Cys Pro Thr Asp Cys Phe Arg Lys
            580                 585                 590
```

-continued

His Pro Asp Ala Thr Tyr Ile Lys Cys Gly Ser Gly Pro Trp Leu Thr
            595                 600                 605

Pro Lys Cys Leu Val His Tyr Pro Tyr Arg Leu Trp His Tyr Pro Cys
        610                 615                 620

Thr Val Asn Phe Thr Ile Phe Lys Ile Arg Met Tyr Val Gly Gly Val
625                 630                 635                 640

Glu His Arg Leu Thr Ala Ala Cys Asn Phe Thr Arg Gly Asp Arg Cys
                645                 650                 655

Asp Leu Glu Asp Arg Asp Arg Ser Gln Leu Ser Pro Leu Leu His Ser
            660                 665                 670

Thr Thr Glu Trp Ala Ile Leu Pro Cys Thr Tyr Ser Asp Leu Pro Ala
        675                 680                 685

Leu Ser Thr Gly Leu Leu His Leu His Gln Asn Ile Val Asp Val Gln
            690                 695                 700

Tyr Met Tyr Gly Leu Ser Pro Ala Ile Thr Lys Tyr Val Val Arg Trp
705                 710                 715                 720

Glu Trp Val Val Leu Leu Phe Leu Leu Leu Ala Asp Ala Arg Val Cys
                725                 730                 735

Ala Cys Leu Trp Met Leu Ile Leu Leu Gly Gln Ala Glu Ala Ala Leu
            740                 745                 750

Glu Lys Leu Val Val Leu His Ala Ala Ser Ala Ala Asn Cys His Gly
        755                 760                 765

Leu Leu Tyr Phe Ala Ile Phe Phe Val Ala Ala Trp His Ile Arg Gly
            770                 775                 780

Arg Val Val Pro Leu Thr Thr Tyr Cys Leu Thr Gly Leu Trp Pro Phe
785                 790                 795                 800

Cys Leu Leu Leu Met Ala Leu Pro Arg Gln Ala Tyr Ala Tyr Asp Ala
                805                 810                 815

Pro Val His Gly Gln Ile Gly Val Gly Leu Leu Ile Leu Ile Thr Leu
            820                 825                 830

Phe Thr Leu Thr Pro Gly Tyr Lys Thr Leu Leu Gly Gln Cys Leu Trp
        835                 840                 845

Trp Leu Cys Tyr Leu Leu Thr Leu Gly Glu Ala Met Ile Gln Glu Trp
            850                 855                 860

Val Pro Pro Met Gln Val Arg Gly Gly Arg Asp Gly Ile Ala Trp Ala
865                 870                 875                 880

Val Thr Ile Phe Cys Pro Gly Val Val Phe Asp Ile Thr Lys Trp Leu
                885                 890                 895

Leu Ala Leu Leu Gly Pro Ala Tyr Leu Leu Arg Ala Ala Leu Thr His
            900                 905                 910

Val Pro Tyr Phe Val Arg Ala His Ala Leu Ile Arg Val Cys Ala Leu
        915                 920                 925

Val Lys Gln Leu Ala Gly Gly Arg Tyr Val Gln Val Ala Leu Leu Ala
            930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
        995                 1000                1005

Arg Leu Gly Gln Glu Ile Leu Leu Gly Pro Ala Asp Gly Tyr Thr

```
                1010                1015                1020

Ser Lys Gly Trp Lys Leu Leu Ala Pro Ile Thr Ala Tyr Ala Gln
    1025                1030                1035

Gln Thr Arg Gly Leu Leu Gly Ala Ile Val Val Ser Met Thr Gly
    1040                1045                1050

Arg Asp Arg Thr Glu Gln Ala Gly Glu Val Gln Ile Leu Ser Thr
    1055                1060                1065

Val Ser Gln Ser Phe Leu Gly Thr Thr Ile Ser Gly Val Leu Trp
    1070                1075                1080

Thr Val Tyr His Gly Ala Gly Asn Lys Thr Leu Ala Gly Leu Arg
    1085                1090                1095

Gly Pro Val Thr Gln Met Tyr Ser Ser Ala Glu Gly Asp Leu Val
    1100                1105                1110

Gly Trp Pro Ser Pro Pro Gly Thr Lys Ser Leu Glu Pro Cys Lys
    1115                1120                1125

Cys Gly Ala Val Asp Leu Tyr Leu Val Thr Arg Asn Ala Asp Val
    1130                1135                1140

Ile Pro Ala Arg Arg Gly Asp Lys Arg Gly Ala Leu Leu Ser
    1145                1150                1155

Pro Arg Pro Ile Ser Thr Leu Lys Gly Ser Ser Gly Pro Val
    1160                1165                1170

Leu Cys Pro Arg Gly His Val Val Gly Leu Phe Arg Ala Ala Val
    1175                1180                1185

Cys Ser Arg Gly Val Ala Lys Ser Ile Asp Phe Ile Pro Val Glu
    1190                1195                1200

Thr Leu Asp Val Val Thr Arg Ser Pro Thr Phe Ser Asp Asn Ser
    1205                1210                1215

Thr Pro Pro Ala Val Pro Gln Thr Tyr Gln Val Gly Tyr Leu His
    1220                1225                1230

Ala Pro Thr Gly Ser Gly Lys Ser Thr Lys Val Pro Val Ala Tyr
    1235                1240                1245

Ala Ala Gln Gly Tyr Lys Val Leu Val Leu Asn Pro Ser Val Ala
    1250                1255                1260

Ala Thr Leu Gly Phe Gly Ala Tyr Leu Ser Lys Ala His Gly Ile
    1265                1270                1275

Asn Pro Asn Ile Arg Thr Gly Val Arg Thr Val Met Thr Gly Glu
    1280                1285                1290

Ala Ile Thr Tyr Ser Thr Tyr Gly Lys Phe Leu Ala Asp Gly Gly
    1295                1300                1305

Cys Ala Ser Gly Ala Tyr Asp Ile Ile Ile Cys Asp Glu Cys His
    1310                1315                1320

Ala Val Asp Ala Thr Ser Ile Leu Gly Ile Gly Thr Val Leu Asp
    1325                1330                1335

Gln Ala Glu Thr Ala Gly Val Arg Leu Thr Val Leu Ala Thr Ala
    1340                1345                1350

Thr Pro Pro Gly Ser Val Thr Thr Pro His Pro Asp Ile Glu Glu
    1355                1360                1365

Val Gly Leu Gly Arg Glu Gly Glu Ile Pro Phe Tyr Gly Arg Ala
    1370                1375                1380

Ile Pro Leu Ser Cys Ile Lys Gly Gly Arg His Leu Ile Phe Cys
    1385                1390                1395

His Ser Lys Lys Lys Cys Asp Glu Leu Ala Ala Ala Leu Arg Gly
    1400                1405                1410
```

```
Met Gly Leu Asn Ala Val Ala Tyr Tyr Arg Gly Leu Asp Val Ser
1415                1420                1425

Ile Ile Pro Ala Gln Gly Asp Val Val Val Ala Thr Asp Ala
1430                1435                1440

Leu Met Thr Gly Tyr Thr Gly Asp Phe Asp Ser Val Ile Asp Cys
1445                1450                1455

Asn Val Ala Val Thr Gln Ala Val Asp Phe Ser Leu Asp Pro Thr
1460                1465                1470

Phe Thr Ile Thr Thr Gln Thr Val Pro Gln Asp Ala Val Ser Arg
1475                1480                1485

Ser Gln Arg Arg Gly Arg Thr Gly Arg Gly Arg Gln Gly Thr Tyr
1490                1495                1500

Arg Tyr Val Ser Thr Gly Glu Arg Ala Ser Gly Met Phe Asp Ser
1505                1510                1515

Val Val Leu Cys Glu Cys Tyr Asp Ala Gly Ala Ala Trp Tyr Asp
1520                1525                1530

Leu Thr Pro Ala Glu Thr Thr Val Arg Leu Arg Ala Tyr Phe Asn
1535                1540                1545

Thr Pro Gly Leu Pro Val Cys Gln Asp His Leu Glu Phe Trp Glu
1550                1555                1560

Ala Val Phe Thr Gly Leu Thr His Ile Asp Ala His Phe Leu Ser
1565                1570                1575

Gln Thr Lys Gln Ala Gly Glu Asn Phe Ala Tyr Leu Val Ala Tyr
1580                1585                1590

Gln Ala Thr Val Cys Ala Arg Ala Lys Ala Pro Pro Pro Ser Trp
1595                1600                1605

Asp Ala Met Trp Lys Cys Leu Ala Arg Leu Lys Pro Thr Leu Ala
1610                1615                1620

Gly Pro Thr Pro Leu Leu Tyr Arg Leu Gly Pro Ile Thr Asn Glu
1625                1630                1635

Val Thr Leu Thr His Pro Gly Thr Lys Tyr Ile Ala Thr Cys Met
1640                1645                1650

Gln Ala Asp Leu Glu Val Met Thr Ser Thr Trp Val Leu Ala Gly
1655                1660                1665

Gly Val Leu Ala Ala Val Ala Ala Tyr Cys Leu Ala Thr Gly Cys
1670                1675                1680

Val Ser Ile Ile Gly Arg Leu His Val Asn Gln Arg Val Val Val
1685                1690                1695

Ala Pro Asp Lys Glu Val Leu Tyr Glu Ala Phe Asp Glu Met Glu
1700                1705                1710

Glu Cys Ala Ser Arg Ala Ala Leu Ile Glu Glu Gly Gln Arg Ile
1715                1720                1725

Ala Glu Met Leu Lys Ser Lys Ile Gln Gly Leu Leu Gln Gln Ala
1730                1735                1740

Ser Lys Gln Ala Gln Asp Ile Gln Pro Ala Met Gln Ala Ser Trp
1745                1750                1755

Pro Lys Val Glu Gln Phe Trp Ala Arg His Met Trp Asn Phe Ile
1760                1765                1770

Ser Gly Ile Gln Tyr Leu Ala Gly Leu Ser Thr Leu Pro Gly Asn
1775                1780                1785

Pro Ala Val Ala Ser Met Met Ala Phe Ser Ala Ala Leu Thr Ser
1790                1795                1800

Pro Leu Ser Thr Ser Thr Thr Ile Leu Leu Asn Ile Met Gly Gly
1805                1810                1815
```

```
Trp Leu Ala Ser Gln Ile Ala Pro Pro Ala Gly Ala Thr Gly Phe
    1820            1825            1830

Val Val Ser Gly Leu Val Gly Ala Ala Val Gly Ser Ile Gly Leu
    1835            1840            1845

Gly Lys Val Leu Val Asp Ile Leu Ala Gly Tyr Gly Ala Gly Ile
    1850            1855            1860

Ser Gly Ala Leu Val Ala Phe Lys Ile Met Ser Gly Glu Lys Pro
    1865            1870            1875

Ser Met Glu Asp Val Ile Asn Leu Leu Pro Gly Ile Leu Ser Pro
    1880            1885            1890

Gly Ala Leu Val Val Gly Val Ile Cys Ala Ala Ile Leu Arg Arg
    1895            1900            1905

His Val Gly Pro Gly Glu Gly Ala Val Gln Trp Met Asn Arg Leu
    1910            1915            1920

Ile Ala Phe Ala Ser Arg Gly Asn His Val Ala Pro Thr His Tyr
    1925            1930            1935

Val Thr Glu Ser Asp Ala Ser Gln Arg Val Thr Gln Leu Leu Gly
    1940            1945            1950

Ser Leu Thr Ile Thr Ser Leu Leu Arg Arg Leu His Asn Trp Ile
    1955            1960            1965

Thr Glu Asp Cys Pro Ile Pro Cys Ser Gly Ser Trp Leu Arg Asp
    1970            1975            1980

Val Trp Asp Trp Val Cys Thr Ile Leu Thr Asp Phe Lys Asn Trp
    1985            1990            1995

Leu Thr Ser Lys Leu Phe Pro Lys Leu Pro Gly Leu Pro Phe Ile
    2000            2005            2010

Ser Cys Gln Lys Gly Tyr Lys Gly Val Trp Ala Gly Thr Gly Ile
    2015            2020            2025

Met Thr Thr Arg Cys Pro Cys Gly Ala Asn Ile Ser Gly Asn Val
    2030            2035            2040

Arg Leu Gly Ser Met Arg Ile Thr Gly Pro Lys Thr Cys Met Asn
    2045            2050            2055

Thr Trp Gln Gly Thr Phe Pro Ile Asn Cys Tyr Thr Glu Gly Gln
    2060            2065            2070

Cys Ala Pro Lys Pro Pro Thr Asn Tyr Lys Thr Ala Ile Trp Arg
    2075            2080            2085

Val Ala Ala Ser Glu Tyr Ala Glu Val Thr Gln His Gly Ser Tyr
    2090            2095            2100

Ser Tyr Val Thr Gly Leu Thr Thr Asp Asn Leu Lys Ile Pro Cys
    2105            2110            2115

Gln Leu Pro Ser Pro Glu Phe Phe Ser Trp Val Asp Gly Val Gln
    2120            2125            2130

Ile His Arg Phe Ala Pro Thr Pro Lys Pro Phe Phe Arg Asp Glu
    2135            2140            2145

Val Ser Phe Cys Val Gly Leu Asn Ser Tyr Ala Val Gly Ser Gln
    2150            2155            2160

Leu Pro Cys Glu Pro Glu Pro Asp Ala Asp Val Leu Arg Ser Met
    2165            2170            2175

Leu Thr Asp Pro Pro His Ile Thr Ala Glu Thr Ala Ala Arg Arg
    2180            2185            2190

Leu Ala Arg Gly Ser Pro Pro Ser Glu Ala Ser Ser Ser Val Ser
    2195            2200            2205

Gln Leu Ser Ala Pro Ser Leu Arg Ala Thr Cys Thr Thr His Ser
```

-continued

```
            2210                2215                2220
Asn Thr Tyr Asp Val Asp Met Val Asp Ala Asn Leu Leu Met Glu
    2225                2230                2235
Gly Gly Val Ala Gln Thr Glu Pro Glu Ser Arg Val Pro Val Leu
    2240                2245                2250
Asp Phe Leu Glu Pro Met Ala Glu Glu Glu Ser Asp Leu Glu Pro
    2255                2260                2265
Ser Ile Pro Ser Glu Cys Met Leu Pro Arg Ser Gly Phe Pro Arg
    2270                2275                2280
Ala Leu Pro Ala Trp Ala Arg Pro Asp Tyr Asn Pro Pro Leu Val
    2285                2290                2295
Glu Ser Trp Arg Arg Pro Asp Tyr Gln Pro Pro Thr Val Ala Gly
    2300                2305                2310
Cys Ala Leu Pro Pro Pro Lys Lys Ala Pro Thr Pro Pro Pro Arg
    2315                2320                2325
Arg Arg Arg Thr Val Gly Leu Ser Glu Ser Thr Ile Ser Glu Ala
    2330                2335                2340
Leu Gln Gln Leu Ala Ile Lys Thr Phe Gly Gln Pro Pro Ser Ser
    2345                2350                2355
Gly Asp Ala Gly Ser Ser Thr Gly Ala Gly Ala Ala Glu Ser Gly
    2360                2365                2370
Gly Pro Thr Ser Pro Gly Glu Pro Ala Pro Ser Glu Thr Gly Ser
    2375                2380                2385
Ala Ser Ser Met Pro Pro Leu Glu Gly Glu Pro Gly Asp Pro Asp
    2390                2395                2400
Leu Glu Ser Asp Gln Val Glu Leu Gln Pro Pro Gln Gly Gly
    2405                2410                2415
Gly Val Ala Pro Gly Ser Gly Ser Gly Ser Trp Ser Thr Cys Ser
    2420                2425                2430
Glu Glu Asp Asp Thr Thr Val Cys Cys Ser Met Ser Tyr Ser Trp
    2435                2440                2445
Thr Gly Ala Leu Ile Thr Pro Cys Ser Pro Glu Glu Glu Lys Leu
    2450                2455                2460
Pro Ile Asn Pro Leu Ser Asn Ser Leu Leu Arg Tyr His Asn Lys
    2465                2470                2475
Val Tyr Cys Thr Thr Ser Lys Ser Ala Ser Gln Arg Ala Lys Lys
    2480                2485                2490
Val Thr Phe Asp Arg Thr Gln Val Leu Asp Ala His Tyr Asp Ser
    2495                2500                2505
Val Leu Lys Asp Ile Lys Leu Ala Ala Ser Lys Val Ser Ala Arg
    2510                2515                2520
Leu Leu Thr Leu Glu Glu Ala Cys Gln Leu Thr Pro Pro His Ser
    2525                2530                2535
Ala Arg Ser Lys Tyr Gly Phe Gly Ala Lys Glu Val Arg Ser Leu
    2540                2545                2550
Ser Gly Arg Ala Val Asn His Ile Lys Ser Val Trp Lys Asp Leu
    2555                2560                2565
Leu Glu Asp Pro Gln Thr Pro Ile Pro Thr Thr Ile Met Ala Lys
    2570                2575                2580
Asn Glu Val Phe Cys Val Asp Pro Ala Lys Gly Gly Lys Lys Pro
    2585                2590                2595
Ala Arg Leu Ile Val Tyr Pro Asp Leu Gly Val Arg Val Cys Glu
    2600                2605                2610
```

-continued

| | | | | | | | | | |
|---|---|---|---|---|---|---|---|---|---|
|Lys|Met|Ala|Leu|Tyr|Asp|Ile|Thr|Gln|Lys|Leu|Pro|Gln|Ala|Val|
| 2615| | | | 2620| | | | 2625| |

Met Gly Ala Ser Tyr Gly Phe Gln Tyr Ser Pro Ala Gln Arg Val
    2630              2635              2640

Glu Tyr Leu Leu Lys Ala Trp Ala Glu Lys Lys Asp Pro Met Gly
    2645              2650              2655

Phe Ser Tyr Asp Thr Arg Cys Phe Asp Ser Thr Val Thr Glu Arg
    2660              2665              2670

Asp Ile Arg Thr Glu Glu Ser Ile Tyr Gln Ala Cys Ser Leu Pro
    2675              2680              2685

Glu Glu Ala Arg Thr Ala Ile His Ser Leu Thr Glu Arg Leu Tyr
    2690              2695              2700

Val Gly Gly Pro Met Phe Asn Ser Lys Gly Gln Thr Cys Gly Tyr
    2705              2710              2715

Arg Arg Cys Arg Ala Ser Gly Val Leu Thr Thr Ser Met Gly Asn
    2720              2725              2730

Thr Ile Thr Cys Tyr Val Lys Ala Leu Ala Ala Cys Lys Ala Ala
    2735              2740              2745

Gly Ile Val Ala Pro Thr Met Leu Val Cys Gly Asp Asp Leu Val
    2750              2755              2760

Val Ile Ser Glu Ser Gln Gly Thr Glu Glu Asp Glu Arg Asn Leu
    2765              2770              2775

Arg Ala Phe Thr Glu Ala Met Thr Arg Tyr Ser Ala Pro Pro Gly
    2780              2785              2790

Asp Pro Pro Arg Pro Glu Tyr Asp Leu Glu Leu Ile Thr Ser Cys
    2795              2800              2805

Ser Ser Asn Val Ser Val Ala Leu Gly Pro Arg Gly Arg Arg Arg
    2810              2815              2820

Tyr Tyr Leu Thr Arg Asp Pro Thr Thr Pro Leu Ala Arg Ala Ala
    2825              2830              2835

Trp Glu Thr Val Arg His Ser Pro Ile Asn Ser Trp Leu Gly Asn
    2840              2845              2850

Ile Ile Gln Tyr Ala Pro Thr Ile Trp Val Arg Met Val Leu Met
    2855              2860              2865

Thr His Phe Phe Ser Ile Leu Met Val Gln Asp Thr Leu Asp Gln
    2870              2875              2880

Asn Leu Asn Phe Glu Met Tyr Gly Ser Val Tyr Ser Val Asn Pro
    2885              2890              2895

Leu Asp Leu Pro Ala Ile Ile Glu Arg Leu His Gly Leu Asp Ala
    2900              2905              2910

Phe Ser Met His Thr Tyr Ser His His Glu Leu Thr Arg Val Ala
    2915              2920              2925

Ser Ala Leu Arg Lys Leu Gly Ala Pro Pro Leu Arg Val Trp Lys
    2930              2935              2940

Ser Arg Ala Arg Ala Val Arg Ala Ser Leu Ile Ser Arg Gly Gly
    2945              2950              2955

Lys Ala Ala Val Cys Gly Arg Tyr Leu Phe Asn Trp Ala Val Lys
    2960              2965              2970

Thr Lys Leu Lys Leu Thr Pro Leu Pro Glu Ala Arg Leu Leu Asp
    2975              2980              2985

Leu Ser Ser Trp Phe Thr Val Gly Ala Gly Gly Gly Asp Ile Phe
    2990              2995              3000

His Ser Val Ser Arg Ala Arg Pro Arg Ser Leu Leu Phe Gly Leu
    3005              3010              3015

```
Leu Leu  Leu Phe Val Gly Val  Gly Leu Phe Leu Leu  Pro Ala Arg
    3020            3025                3030
```

```
<210> SEQ ID NO 12
<211> LENGTH: 13
<212> TYPE: DNA
<213> ORGANISM: Hepatitis C virus

<400> SEQUENCE: 12
ctagccgagt agc                                                               13

<210> SEQ ID NO 13
<211> LENGTH: 26
<212> TYPE: DNA
<213> ORGANISM: Hepatitis C virus

<400> SEQUENCE: 13
ccccggcagg cttatgccta gaattc                                                 26

<210> SEQ ID NO 14
<211> LENGTH: 6
<212> TYPE: PRT
<213> ORGANISM: Hepatitis C virus

<400> SEQUENCE: 14

Pro Arg Gln Ala Tyr Ala
1               5
```

RECOMBINANT HUMAN HEPATITIS C VIRUS-LIKE PARTICLE AND METHOD FOR PRODUCING THE SAME

TECHNICAL FIELD

The present invention relates to a human recombinant hepatitis C virus-like particle and a method for producing the same.

BACKGROUND ART

Methods for introducing a gene into an animal cell are roughly classified into physiochemical methods and biological methods. Examples of physiochemical methods include methods such as calcium phosphate coprecipitation, DEAE dextran, lipofection, microinjection, and electroporation. Examples of biological methods include methods using viral vectors.

A viral vector method is a method in which a gene is introduced by utilizing the cell invasion mechanism of virus, that is, an infecting ability.

Virus-derived structural proteins (nucleocapsid, envelope protein, etc.) exist on the surface of a recombinant viral particle prepared by using a viral vector, which have a mechanism for efficient introduction of a gene so that the virus can infect a cell via a receptor on the cell surface. Therefore, a recombinant viral particle prepared using such a viral vector can be used not only to introduce a gene into an animal cell to generate a cell expressing the gene of interest, but also to perform gene therapy, construct a transgenic animal, and so forth.

Viral vectors are grouped into retrovirus vectors, DNA virus vectors, and RNA virus vectors and characterized by the length of a gene that can be introduced, whether the gene is incorporated into the chromosomal genome in a cell, whether the gene can only be introduced into a dividing cell or can also be introduced into a nondividing cell, types of cells that can be infected, cytotoxicity, gene introduction efficiency, and so forth, which depend on the type of the original virus.

Retroviruses have a plus-strand RNA as a genome. This RNA has properties characteristic to mRNA of eukaryotic cells, specifically, a methylated cap structure at the 5' end and a polyA tail of about 200 nucleotides at the 3' end. In an infected cell, this RNA is converted to DNA by reverse transcriptase of the virus. Further, the DNA is incorporated into genomic DNA of the host by actions of enzymes encoded by the viral genes. The incorporated DNA is called provirus. A repetitive sequence (long terminal repeat: LTR) occurs at the either end of a provirus, and viral RNA is synthesized by a promoter existing in this sequence. Viral proteins are translated from the synthesized RNA, and a genome-sized RNA is incorporated into the viral particle, which is released out of the cell as a daughter particle.

The RNA structure required for production of a viral particle includes LTR at either end, a primer-binding site sandwiched therebetween, a packaging signal, and a polypurine signal. These are essential cis factors. On the other hand, genes coding for viral proteins are not essential as cis factors, and replication and production of a particle normally occur once viral proteins are supplied within the infected cell.

Therefore, to produce a recombinant retrovirus, a vector from which genes encoded by the retrovirus, such as gag, pol, and env, are removed and into which a gene of interest to be expressed is inserted instead (referred to as a retrovirus vector) is prepared, and this vector is introduced into a cell in which viral proteins are supplied (usually referred to as a packaging cell) to prepare a retrovirus particle incorporated with a foreign gene (Non-patent Document 1).

Examples of the retrovirus include mouse leukemia virus, feline leukemia virus, baboon type C oncovirus, human immunodeficiency virus, adult T cell leukemia virus, and so forth. Furthermore, examples of those reported as recombinant retrovirus vectors include those based on mouse leukemia virus (Non-patent Document 1), those based on human immunodeficiency virus (Non-patent Document 2), and so forth.

A system for production of a recombinant retrovirus consists of two component units, specifically, a retrovirus vector carrying genetic information (a foreign gene of interest) to be introduced and all factors required for packaging and incorporation of the viral genome in cis (recombinant retrovirus DNA) and a retrovirus packaging cell that supplies viral proteins encoded by the gag, pol, and env genes. The recombinant retrovirus particle cannot be released by a packaging cell alone into which a recombinant vector expressing the gag, pol, and env genes is introduced.

To produce a recombinant retrovirus particle, the gag, pol, and env proteins need to be positioned in trans. Therefore, by introducing a retrovirus vector into a packaging cell into which a recombinant vector expressing the gag, pol, and env genes is introduced, a recombinant retrovirus carrying genetic information held in the above-mentioned vector can be produced. Subsequently, when a cell is infected with these viruses, the retrovirus vector will be incorporated into the chromosomal genome in the cell according to the natural retrovirus life cycle.

Thus, the retrovirus vector method is a system constructed for the purpose of efficient incorporation of a specific DNA into the chromosomal genome of the host. However, since the location of the gene of interest to be inserted cannot be predicted, possibilities cannot be ruled out that normal gene may be damaged by insertion, genes in the vicinity of the insertion site may be activated, and the foreign gene of interest may be overexpressed or underexpressed. To overcome these problems, development of a transient expression system using a DNA virus vector that can be utilized as an extrachromosomal gene was promoted.

A DNA virus vector is a vector derived from a DNA virus. DNA virus carries DNA in its viral particle as genetic information. This DNA is replicated by repetition of a process of producing a complementary strand using its own DNA as a template by host-derived DNA-dependent DNA replication enzymes at least as a part of catalysts. Examples of DNA virus vectors that can be utilized as an extrachromosomal gene include adenoviral vectors.

Human adenovirus has about 36-kb linear double-stranded DNA as a genome, and regions included in this genome are roughly divided into early genes E1, E2, E3, and E4 and late genes L1, L2, L3, L4, and L5. The early genes are primarily involved in virus replication, and the late genes are involved in synthesis of viral structural proteins such as capsid. An adenovirus vector used for introduction of a gene is prepared by replacing the E1 region (divided into E1A and E1B, and all adenovirus promoters are activated by E1A), an early gene, with a desired foreign gene (gene of interest) and proliferated using 293 cells, a cell line that can supply E1A in trans (293 cells express E1A). An adenovirus vector deficient in the E1A region cannot be proliferated in a normal cell, which does not express E1A. Since the E3 region is not essential for propagation of virus, it is often removed to increase the insertion size of a foreign gene. Since adenovirus can package a genome up to 105% of the genome size of a wild type in its capsid, a foreign gene of up to 8.1 kb can be inserted by deleting the E1 and E3 regions (Non-patent Document 3).

An adenovirus vector can introduce a gene into a nongrowing cell or a growing cell (Non-patent Document 4). Therefore, this method is suitable for in vivo gene introduction methods. One of disadvantages of this vector is the generally short gene expression period (in units of week). This is because the adenovirus genome exists only within an extrachromosomal region (episome) and is not replicated or amplified. A second disadvantage is that the adenovirus commonly used at present causes nonspecific inflammatory reactions and intensifies a cell-mediated immune response against the vector itself. Therefore, it is difficult to perform continuous administration in gene therapy (Non-patent Document 5).

Viral vectors based on RNA virus are being developed. RNA virus is replicated by repeating the process of generating a complementary strand using its own RNA as a template by its own RNA-dependent RNA replication enzymes as catalysts.

RNA viruses are classified into minus-strand RNA viruses and plus-strand RNA viruses. Representative examples of minus-strand RNA viruses include influenza virus. The influenza virus genome consists of eight minus-strand RNA segments. When influenza virus infects a cell, gene transcription is initiated by proteins in the influenza particle. First, viral RNA polymerase cleaves mRNA of the host cell at a dozen or so nucleotides from the 5'-end cap structure and utilizes the fragments as primers to elongate the RNA strand (plus strand). Viral proteins are translated from this plus-strand RNA. In the replication process, RNA completely complementary to the viral RNA is synthesized, and progeny virus RNA is amplified using this sequence as a template. Then, the viral RNA is packaged together with viral proteins to form a viral particle.

Therefore, to produce influenza virus in a cell culture system, proteins encoded by influenza virus are expressed by RNA polymerase II promoters such as, for example, CMV and CAG promoters, viral RNA is expressed by RNA polymerase I promoters, promoters without a cap structure and polyA, such as, for example, rRNA gene promoters, and the viral RNA is packaged together with viral proteins in the cell to form a viral particle (Non-patent Document 6). However, the amount of virus to be produced is not specified, and this technique has not been established as a technique that can be utilized in view of production to a satisfactory extent.

Examples of viruses classified as plus-strand RNA viruses include Sindbis virus and hepatitis C virus. The genome RNA of a plus-strand RNA virus also functions as messenger RNA (hereinafter referred to as "mRNA") at the same time and can produce proteins required for replication and particle formation depending on the translation function of the host cell. In other words, the genome RNA of the plus-strand RNA virus itself has a transmitting ability.

Viral vectors derived from Sindbis virus has a basic structure of the genome RNA from which the structural gene region involved in the virus structure is deleted and in which a gene group for proteins required for virus transcription and replication are retained and RNA in which a desired foreign gene is ligated to the downstream of the transcription promoter. When such RNA or cDNA transcribed to this RNA is introduced into a cell, autonomous replication of RNA vector including the foreign gene and transcription of the foreign gene located downstream of the transcription promoter occur, and a foreign gene product of interest is expressed in the cell. Further, a complex that has an infecting ability but not a transmitting ability can be prepared by allowing a cDNA unit expressing structural genes (helper) and a cDNA unit expressing the above-mentioned RNA vector to coexist in a packaging cell (Non-patent Document 7).

Since Sindbis virus uses 67-kDa high-affinity laminin receptor (LAMR) as a receptor and infects nerve cells in high efficiency, Sindbis virus vector draws attention as a system for introducing a gene specifically to nerves (Non-patent Document 8). However, since it has been shown that infection by Sindbis virus induces apoptosis of the host cell (Non-patent Document 9), toxicity is concerned.

The genome of hepatitis C virus (HCV) is plus-strand single-stranded RNA of about 9600 nucleotides. This genome RNA comprises the 5' untranslated region (also expressed as 5'NTR or 5'UTR), the translated region including a structural region and a nonstructural region, and the 3' untranslated region (also expressed as 3'NTR or 3'UTR). Structural proteins of HCV are encoded in the structural region, and multiple nonstructural proteins are encoded in the nonstructural region.

Such structural proteins (Core, E1, E2, and p7) and nonstructural proteins (NS2, NS3, NS4A, NS4B, NS5A, and NS5B) of HCV are translated as a continuous polyprotein from the translated region, subjected to limited digestion by protease, released, and produced. Of these structural proteins and nonstructural proteins (i.e., viral proteins of HCV), Core is the core protein. E1 and E2 are envelope proteins. Nonstructural proteins are viral proteins involved in replication of the virus itself. NS2 is known to have a metalloprotease activity, and NS3 is known to have a serine protease activity (1/3 on the side of the N terminus) and a helicase activity (2/3 on the side of the C terminus). Furthermore, it is also reported that NS4A is a cofactor for the protease activity of NS3, and that NS5B has an RNA-dependent RNA polymerase activity.

It has been revealed that HCV is classified into many types depending on the genotype or the serotype. According to the phylogenetic analysis method by Simmonds et al. using nucleotide sequences of HCV strains, which is a currently mainstream HCV genotype classification method, HCV is classified into six types including genotypes 1a, 1b, 2a, 2b, 3a, and 3b, and these are further subdivided into several subtypes. Furthermore, the nucleotide sequences of the full-length genomes of some genotypes of HCV have been determined (Non-patent Documents 10 to 13).

An HCV particle is captured by sulfated polysaccharides on the cell surface, binds to a high-affinity receptor via envelope proteins, and is taken up into the endosome by endocytosis. Then, the virus membrane and the endosome membrane fuse, and the nucleocapsid invades the cytoplasm. Translation of the naked viral genome is initiated by Internal Ribosome Entry Site (IRES). Translation and cleavage of a protein occur on the endoplasmic reticulum membrane. The Core protein, the E1 and E2 proteins, and viral RNA replicated on the endoplasmic reticulum are assembled to form a viral particle. Then, the particle buds into the endoplasmic reticulum lumen. It is thought that the particle that has budded is released out of the cell through the Golgi apparatus.

Recently, preparation of an HCV subgenomic RNA replicon as HCV-derived RNA having an autonomous replication ability (Patent Documents 1 and 2 and Non-patent Documents 14 to 16) has enabled analysis of the HCV replication mechanism using cultured cells. This HCV subgenomic RNA replicon is obtained by replacing the structural proteins existing downstream of HCV IRES in the 5' untranslated region of HCV genomic RNA with the neomycin resistance gene and EMCV-IRES ligated to the downstream thereof. It has been demonstrated that, when introduced into human liver cancer cell Huh7 and cultured in the presence of neomycin, this RNA replicon autonomously replicates in the Huh7 cell. Furthermore, it has been demonstrated that some HCV subgenomic RNA replicons autonomously replicate not only in Huh7 but also in cells such as human cervical cancer cell HeLa or human liver cancer cell HepG2 (Patent Document 3). Furthermore, Patent Document 2 proposes production of HCV virus particle utilizing the full-length HCV genome when a recombinant HCV is used as a vector for gene therapy.

[Patent Document 1] JP Patent Publication (Kokai) No. 2002-171978 A

[Patent Document 2] JP Patent Publication (Kokai) No. 2001-17187 A

[Patent Document 3] International Patent Publication WO2004/104198

[Non-patent Document 1] Mann, R. et al., Cell, 33 (1983) p 153-59

[Non-patent Document 2] Simada, T et al., J Clin Invest. 88 (1991) p 1043-47

[Non-patent Document 3] Betta, A et al., Proc. Natl. Acad. Sci. USA 91 (1994) p 8802-06

[Non-patent Document 4] Burden, S & Yarden, Y., Neuron, 18 (1997) p 847-55

[Non-patent Document 5] Crystal, R. G Science, 270, (1995) p 404-10

[Non-patent Document 6] Neumann, G. & Kawaoka, Y., Virology 287 (2001) p 243-50

[Non-patent Document 7] Berglund, P et al., Biotechnology, 11 (1993) p 916-920

[Non-patent Document 8] Wang, K. S et al., J. Virol. 66 (1992) p 4992-5001

[Non-patent Document 9] Levine, B. et al., Nature, 361 (1993) p 739-42

[Non-patent Document 10] Simmonds, P. et al., Hepatology, 10 (1994) p 1321-24

[Non-patent Document 11] Choo, Q. L et al., Science, 244 (1989) p 359-362

[Non-patent Document 12] Okamoto, H et al., J. Gen. Virol., 73 (1992) p 673-79

[Non-patent Document 13] Mori, S. et al., Biochem. Biophis. Res. Commun. 183 (1992)

[Non-patent Document 14] Blight et al., Science, 290 (2000) p 1972-74

[Non-patent Document 15] Friebe et al., J. Virol., 75 (2001) p 12047-57

[Non-patent Document 16] Kato, T. et al., Gastroenterology, 125 (2003) p 1808-17

DISCLOSURE OF THE INVENTION

HCV has not actually been developed as a viral vector like those of retrovirus, adenovirus, influenza virus, and Sindbis virus. If such an HCV vector is developed, genes can be introduced specifically into cells of tissues of the liver or the like. In this case, to ensure safety to a higher extent, it is desiable that the HCV vector infects cells but does not have a transmitting property.

An object of the present invention is to develop a recombinant hepatitis C virus (HCV)-like particle that is usable as such a vector as described above. Furthermore, another object of the present invention is to provide a method for producing this HCV-like particle efficiently.

The inventors of the present invention attempted to allow cultured cells to produce a recombinant HCV-like particle that appears to be industrially useful in view of safety, convenience, and applicability. First, the HCV genome was divided into a vector expressing the HCV structural proteins and a vector including the genes involved in replication. A desired foreign gene and/or IRES (Internal Ribosome Entry Site) can be included in the latter vector.

The inventors of the present invention constructed a vector obtained by cloning DNA including a desired foreign gene, the IRES sequence, and the genes involved in replication of HCV into the downstream of the T7 promoter and synthesized in vitro an HCV subgenomic RNA replicon including the foreign gene sequence using T7 polymerase. This RNA replicon was introduced into a cultured animal cell to obtain a cell strain in which the HCV subgenomic RNA replicon was replicated.

Subsequently, they found a system that can introduce a vector highly expressing the HCV structural proteins into the cell strain in high efficiency and introduced it into cells carrying HCV subgenomic RNA replicons of various genotypes. As a result, by expressing the HCV structural proteins in cells, they successfully found combinations with which the HCV subgenomic RNA replicon can be packaged in a viral particle.

Furthermore, the inventors of the present invention confirmed that a recombinant HCV-like particle produced by the method of the present invention infects cells and that a cell infected by the recombinant HCV does not have a transmitting property, producing no daughter viral particle. Due to such characteristics, the recombinant HCV particle of the present invention can be used as a vector for introduction of a foreign gene or for gene therapy.

Specifically, the present invention is characterized by the following characteristics in summary.

As a first aspect, the present invention provides a method for producing a recombinant hepatitis C virus particle, comprising the steps of introducing into:

(i) a cell carrying an RNA replicon having a nucleotide sequence comprising the 5' untranslated region, the nucleotide sequence coding for the NS3, NS4A, NS4B, NS5A, and NS5B proteins and the 3' untranslated region of genome RNA derived from a hepatitis C virus strain, (ii) a vector expressing the Core, E1, E2, and p7 proteins derived from a hepatitis C virus strain that is the same as or different from the strain as defined in the above (i), culturing the cell, and recovering the produced recombinant hepatitis C virus particle.

As one embodiment, the hepatitis C virus strain of the above (i) and (ii) is at least one strain independently selected from the group consisting of virus strains of genotypes 1a, 1b, 2a, 2b, 3a, and 3b.

In another embodiment, the hepatitis C virus strain of the above (i) and (ii) is at least one strain independently selected from the group consisting of virus strains of genotypes 1b and 2a.

Furthermore, in another embodiment, the hepatitis C virus strain of the above (i) is a virus strain of genotype 1b.

In a preferred embodiment, the above-mentioned virus strain of genotype 1b is the con1 strain or a strain derived therefrom.

In another embodiment, the hepatitis C virus strain of the above (ii) is a virus strain of genotype 2a.

In a preferred embodiment, the above-mentioned virus strain of genotype 2a is the JFH1 strain or a strain derived therefrom.

In yet another embodiment, the above-mentioned RNA replicon can further include at least one IRES sequence.

In yet another embodiment, the above-mentioned RNA replicon can further include at least one foreign gene.

In a preferred embodiment, the above-mentioned IRES and the above-mentioned foreign gene can be positioned between the above-mentioned 5' untranslated region and the above-mentioned NS3.

In yet another embodiment, the above-mentioned cell is an animal cell.

In a preferred embodiment, the above-mentioned animal cell is a mammal cell.

Examples of the above mammal cell include Huh7, HepG2, and established cell lines derived from these cells.

In yet another embodiment, the above-mentioned expression vector is a viral vector.

In a preferred embodiment, the above-mentioned viral vector is a vaccinia virus vector.

Viral particles can be proliferated by allowing the recombinant hepatitis C virus particle produced and recovered by the above-described method of the present invention to infect HCV-susceptible cells such as hepatic or lymphoid cells. Such processes are encompassed in the scope of the present invention includes.

According to a second aspect, the present invention also provides a recombinant hepatitis C virus particle produced by the above-described method of the present invention and characterized by having an infecting ability but not a transmitting ability.

In one embodiment thereof, a foreign gene is introduced into the above-mentioned recombinant hepatitis C virus particle in an expressible manner.

In another embodiment, the above-mentioned recombinant hepatitis C virus particle is a vector.

In the present invention, one of preferred methods for producing a recombinant hepatitis C virus particle is a method for producing a recombinant hepatitis C virus particle, wherein said method comprises the steps of introducing into (i) a cell in which an RNA replicon consisting of a nucleotide sequence comprising at least the 5' untranslated region, the nucleotide sequence coding for the NS3, NS4A, NS4B, NS5A, and NS5B proteins, and the 3' untranslated region of a genome RNA derived from the hepatitis C virus con1 strain, or an RNA replicon further containing at least one foreign gene and/or at least one IRES sequence in addition to the nucleotide sequence, autonomously replicates (ii) a vaccinia virus vector expressing the Core, E1, E2, and p7 proteins of hepatitis C virus derived from the JFH1 strain, culturing the cell, and recovering the produced recombinant hepatitis C virus particle.

Furthermore, in the present invention, a preferred recombinant hepatitis C virus particle is produced by the above-described preferred method.

The present invention further includes the following [1] and [2].

[1] A method for producing a recombinant hepatitis C virus-like particle comprising the steps of introducing into (i) a cell carrying a RNA replicon comprising a nucleotide sequence comprising the 5' untranslated region, the nucleotide sequence coding for the NS3, NS4A, NS4B, NS5A, and NS5B proteins, and the 3' untranslated region of a genome RNA derived from at least one virus strain selected from the group consisting of hepatitis C virus strains of genotypes 1a, 1b, 2a, 2b, 3a, and 3b, (ii) a vector expressing the Core, E1, E2, and p7 proteins derived from at least one virus strain selected from the group consisting of hepatitis C virus strains of genotypes 1a, 1b, 2a, 2b, 3a, and 3b that is the same as or different from the hepatitis C virus strain as defined in the above (i), culturing the cell, and recovering the produced virus-like particle.

It is preferable in this method that the hepatitis C virus strain of genotype 1b as defined in the above-mentioned (i) is the con1 strain, and that the hepatitis C virus strain of genotype 2a as defined in the above-mentioned (i) is the JFH1 strain.

Furthermore, it is also preferable in this method that the hepatitis C virus strain of genotype 1a as defined in the above-mentioned (ii) is the H77c, 1, H, or HC-J1 strain.

It is also preferable in this method that the hepatitis C virus strain of genotype 1b as defined in the above-mentioned (ii) is the J1, con1, TH, J, JT, and BK strain.

It is also preferable in this method that the hepatitis C virus strain of genotype 2a as defined in the above-mentioned (ii) is the JFH1, HC-J6, JCH1, or J6CF strain.

It is also preferable in this method that the hepatitis C virus strain of genotype 3a as defined in the above-mentioned (ii) is the NZL1, K3a/650, 452, or E-b1 strain.

It is also preferable in this method that the hepatitis C virus strain of genotype 3b as defined in the above-mentioned (ii) is the Tr strain.

Furthermore, it is preferable in this method that the vector of the above-mentioned (ii) is a vaccinia virus vector or an EF-1$\alpha$ promoter carrying vector.

Furthermore, it is preferable in this method that the above-mentioned RNA replicon further comprises at least one internal ribosome entry site (IRES) sequence and/or at least one foreign gene.

It is preferable that the IRES sequence and/or the foreign gene is positioned between the above-mentioned 5' untranslated region and the sequence coding for the above-mentioned NS3 protein.

In this method, the above-mentioned cell is preferably an animal cell. Preferred examples of the animal cell include the Huh7 cell, the HepG2 cell, and established cell lines derived from these cells.

[2] A recombinant hepatitis C virus-like particle produced by the above-described method [1] that has an infecting property but not a transmitting ability.

A recombinant infectious HCV-like particle in which an HCV subgenomic RNA including a desired foreign gene is packaged and which does not have a transmitting property and a production method thereof can be provided by the present invention. Since such a recombinant infectious HCV-like particle has an advantage of not having a transmitting property, it can be used for gene introduction (e.g., gene therapy), in particular, into hepatic or lymphoid cells or tissues or can be used as a viral vector for producing a transgenic animal or as an attenuated vaccine.

BRIEF DESCRIPTION OF THE DRAWINGS

FIG. 1 is a schematic view of an embodiment of the present invention, which shows production processes of a recombinant HCV-like particle. a): HCV subgenomic RNA replicons are replicated in the Huh7 cell into which the HCV subgenomic RNA replicon is introduced. A viral particle is not produced. b): In the cell of a) into which an HCV structural protein expressing vector is introduced, virus-like particles in which the HCV subgenomic RNA replicon is packaged are produced utilizing expressed HCV structural proteins. c): In a cell infected by the virus-like particle produced in b), HCV subgenomic RNA replicon are replicated, but no daughter viral particle is produced.

FIG. 2 shows structural drawings of HCV genomic RNA and cDNA of HCV subgenomic RNA. The upper diagram and the middle diagram show pJFH1 and pSGR-JFH1, respectively, prepared from HCV of genotype 2a. The lower diagram shows 1389/NS3-3'/wt prepared from HCV genotype 1b. The symbols in the figure denote as follows: T7, T7

RNA promoter; 5'UTR, 5' untranslated region; Core, Core protein; E1 and E2, envelope proteins; p7, p7 protein; NS2, NS3, NS4A, NS4B, NS5A, and NS5B, nonstructural proteins; 3'UTR, 3' untranslated region; AgeI, PmeI, and XbaI, cleavage sites of restriction enzymes AgeI, PmeI, and XbaI; EMCV IRES, internal ribosome entry site of encephalomyocarditis virus.

FIG. 3 shows maps of vectors for expressing the HCV structural proteins of the present invention (SEQ ID NOS: 12, 13, and 14). Specifically, the upper diagram shows pGAGC-p7JFH1, a plasmid clone prepared by inserting the JFH structural region genes into the downstream of the CAG promoter. The lower diagram shows the structure of pEF4C-p7JFH1, a plasmid clone prepared by inserting the JFH structural region genes into the downstream of the elongation factor 1α promoter sequence. The symbols in the figure denote as follows: CAG, CAG promoter; pA, additional polyA sequence; EcoRI, cleavage site of restriction enzyme Econ EF-1α, elongation factor 1α promoter; BGH pA, additional polyA sequence of bovine growth factor.

Figure 6:
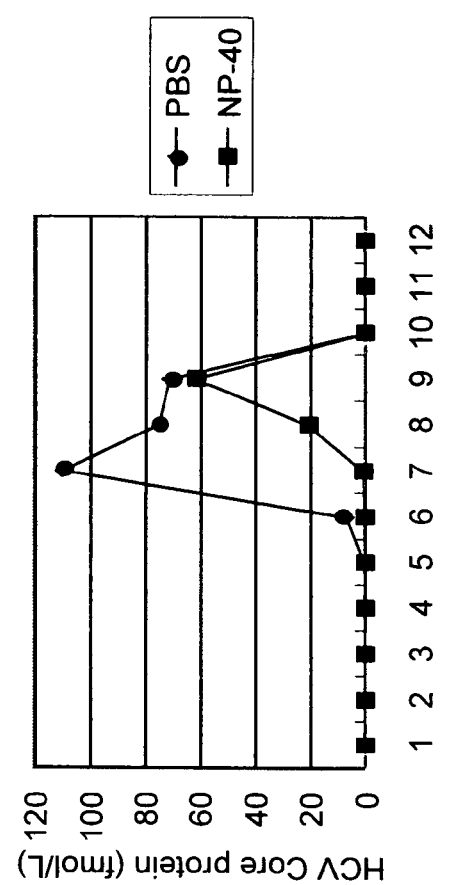
Figure 6:
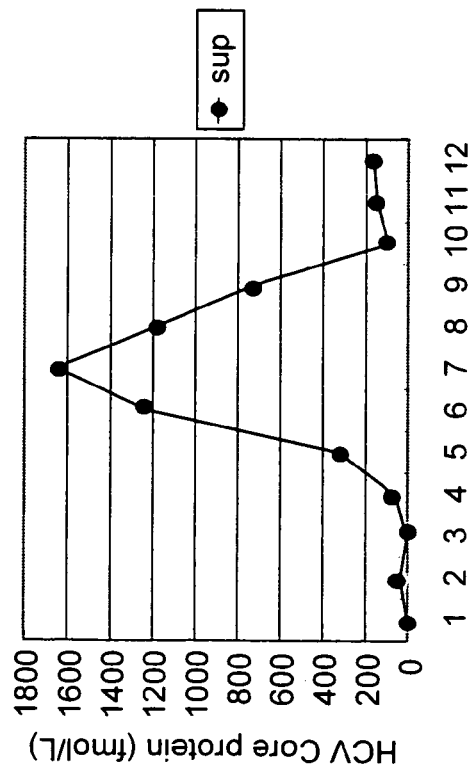

FIG. 6 shows graphs showing the amount of the HCV Core protein (vertical axis) in each fraction (horizontal axis) obtained by allowing DIsJFHst, a vaccinia virus vector, to infect a replicon carrying cell strain 5-15 and fractionating the cell culture supernatant (sup) by a sucrose density gradient. The closed circle represents the HCV Core protein, and the closed square represents results using an NP40-treated culture supernatant. Experiment 1 shows results of only untreated culture (FIG. 6A), and Experiment 2 shows results of untreated and NP40-treated culture supernatants (FIG. 6B).

BEST MODE FOR CARRYING OUT THE INVENTION

1. Definition

The terms used in the present specification have the following meanings.

The term "RNA replicon" refers to RNA that is prepared by modifying the HCV virus genome and has an autonomously replicating ability.

The term "autonomously replicating ability" means an ability of autonomously reproducing copies of a nucleic acid (i.e., replication) in a cell like plasmid DNA.

The term "infecting ability" or "infecting property" refers to an ability of introducing a nucleic acid and the like within a virus into a cell due to abilities of adhering to a cell, fusing with a cell membrane, and the like.

The term "recombinant hepatitis C virus" means a virus obtained by changing properties of the original HCV virus qualitatively/quantitatively using genetic engineering techniques. Examples thereof include a virus capable of expressing a foreign gene in addition to genes expressed by the original virus, a virus deficient in a transmitting property or an ability of replicating a virus genome of the original virus, and so forth. In the broad sense, viruses obtained by recombination of genes between different types or subtypes of the same virus are included.

The term "transmitting property" or "transmitting ability" means an ability of forming an infecting particle or a complex similar thereto and transmitting it into another cell after introduction of a nucleic acid into a cell by infection or an artificial technique and replication of the nucleic acid existing in the cell.

"Core" is a core structural protein of HCV.

"E1" and "E2" are both envelope structural proteins.

"NS" refers to a nonstructural protein of HCV, which is involved in replication of the virus itself. "NS2" has a metalloprotease activity. "NS3" has a serine protease activity (⅓ on the N terminus side) and a helicase activity (⅔ on C terminus side). "NS4A" is a cofactor for the protease activity of NS3. The function of "NS4B" is not clear. "NS5A" is thought to have an activity of regulating transfer of information of the host cell. "NS5B" has an RNA-dependent RNA polymerase activity.

The term "IRES sequence" means an internal ribosome entry site, which can bind the ribosome within RNA to initiate translation.

The expression "in an expressible manner" means a state that a gene of interest can be transcribed and translated by regulatory sequences such as a promoter and an enhancer.

2. HCV Subgenomic RNA Replicon Carrying Cell

The wild type HCV genome consists of about 9.6-kb single-stranded RNA coding for a precursor protein of about 3000 amino acids. The HCV genome is constituted by the 5' untranslated region (5'UTR), Core, E1, E2, p7, NS2, NS3, NS4A, NS4B, NS5A, NS5B, and the 3' untranslated region (3'UTR) in this order. The HCV subgenomic RNA replicon used in the method of the present invention includes modified RNA constituted by the 5' untranslated region, NS3, NS4A, NS4B, NS5A, NS5B, and the 3' untranslated region in this order. This RNA replicon is introduced into a specific cell in an expressible manner so that it can be replicated with actions of regulatory factors such as a promoter.

RNA replicon may further comprise a foreign gene and/or an IRES sequence. The foreign gene and the IRES sequence can be preferably positioned between the 5' untranslated region and the sequence coding for NS3 in the order of the foreign gene and the IRES sequence.

Preferred examples of the IRES sequence include, but are not limited to, EMCV IRES (internal ribosome entry site of encephalomyocarditis virus), FMDV IRES, HCV IRES, and so forth. EMCV IRES and HCV IRES are more preferred, and EMCV IRES is most preferred.

Examples of the foreign gene used include genes showing drug resistance (that is, these genes enable cell selection; cells having this gene will have resistance to the drug) such as, for example, a gene coding for neomycin, hygromycin, puromycin, zeocin, blasticidin, thymidine kinase, kanamycin, or the like; reporter genes (that is, these genes are marker genes that code for a gene product used as an indicator of gene expression) such as, for example, genes coding for an enzyme that catalyses a luminescent reaction or a color reaction of a reporter gene such as, for example, luciferase, green fluorescence protein (GFP), β-galactosidase, and the like; furthermore, target genes of gene therapy and therapeutic nucleic acids such as, for example, genes coding for various proteins useful for the treatment of diseases requiring treatment in mammals including humans such as, for example, enzymes, cytokines, chemokines, hormones, antibodies, immunoregulatory molecules, tumor suppressing proteins, growth factors, membrane proteins, and vasoactive proteins, therapeutic nucleic acids such as antisense RNA and siRNA, and so forth.

Figure 2:
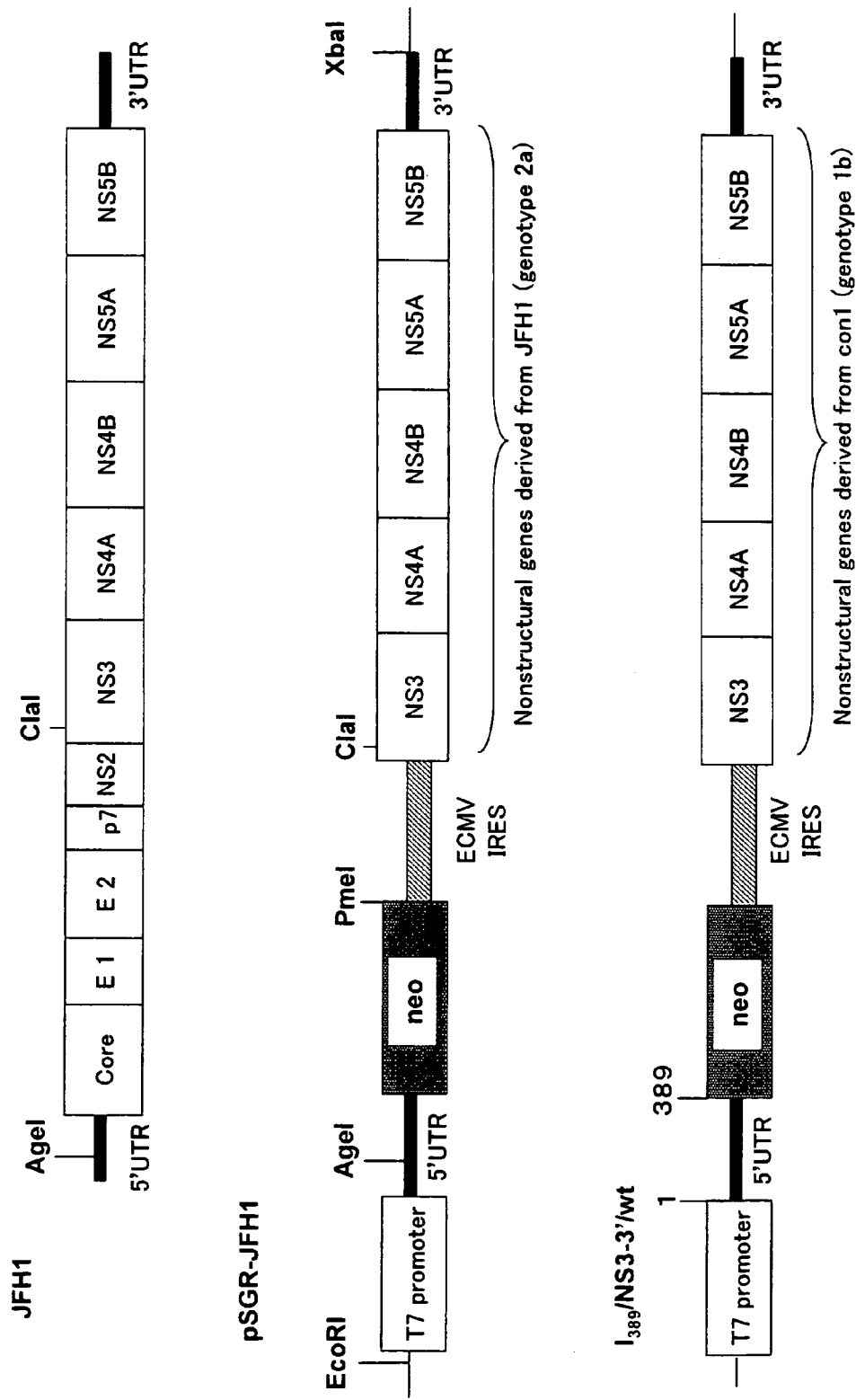

Specific examples of the HCV subgenomic RNA replicon include pSGR-JFH1 (middle diagram in FIG. 2), $I_{389}$/NS3-3'/wt (lower diagram in FIG. 2), and so forth. Such HCV subgenomic RNA replicons can be prepared by the methods described in, for example, Kato, T. et al. Gastroenterology, 125 (2003) p 1808-1817, a publication by the inventors of the present invention, International Patent Publication WO2004/104198 (Patent Document 3), and so forth.

In the phylogenetic analysis method using nucleotide sequences of an HCV strains, HCV is classified into six types: genotypes 1a, 1b, 2a, 2b, 3a, and 3b. Each of these types is further classified into several subtypes. The full-length nucleotide sequences of the HCV genomes of some genotypes have been determined (Simmonds, P. et al., Hepatology, 10 (1994) p 1321-1324; Choo, Q. L et al., Science, 244 (1989) p 359-362; Okamoto, H. et al., J. Gen. Virol., 73 (1992) p 673-679; Mori, S. et al., Biochem. Biophis. Res. Commun. 183 (1992) p 334-342; and International Patent Publication WO2004/104198).

Specific examples of the HCV strains of genotype 1a include the H77c strain (consensus sequence of the H77 strain: GenBank accession number AF011751), the 1 strain (GenBank accession number M62321), H strain (GenBank accession number M67463), the HC-J1 strain (GenBank accession number D10749), and so forth. Specific examples of the HCV strains of genotype 1b include the J1 strain (GenBank accession number D89815), the con1 strain (GenBank accession number AJ238799, may be referred to as the Con-1 strain), the TH strain (Wakita, T. et al., J. Biol. Chem., 269 (1994) p 14205-14210), the J strain (GenBank accession number D90208), the JT strain (GenBank accession number D0171), the BK strain (GenBank accession number M58335), and so forth. Specific examples of the HCV strains of genotype 2a include the JFH1 strain (GenBank accession number AB047639, may be referred to as the JFH-1 strain), the HC-J6 strain (GenBank accession number D00944), the JCH1 strain (GenBank accession number AB047640), the J6CF strain (GenBank accession number AF177036), and so forth. Specific examples of the HCV strains of genotype 2b include the HC-J8 strain (GenBank accession number D01221) and so forth. Specific examples of the HCV strains of genotype 3a include the NZL1 strain (GenBank accession number D17763), the K3a/650 strain (GenBank accession number D28917), the 452 strain (GenBank accession number DQ437509), the E-b1 strain (Chan, S. et al., J. Gen. Virol., 73 (1992) p 1131-1141), and so forth. Specific examples of the HCV strains of genotype 3b include the Tr strain (Chayama, K. et al., J. Gen. Virol., 75 (1994) p 3623-3628) and so forth. Furthermore, a list of GenBank accession numbers for other strains has also already been reported (Tokita, T. et al., J. Gen. Virol. 79 (1998) p 1847-1857; Cristina J. & Colina R. Virolgy Journal, 3 (2006) p 1-8).

The elements constituting the HCV subgenomic RNA replicon used in the present invention (specifically, 5' untranslated region, NS3, NS4A, NS4B, NS5A, NS5B, and 3' untranslated region) may be derived from any strain of the above-mentioned genotypes or subtypes thereof so long as the HCV subgenomic RNA replicon can be constructed so that it can be replicated in a cell. It is noted that the present invention is a method for producing a recombinant hepatitis C virus-like particle that has an infecting property but not a transmitting property, and it is preferable that the RNA replicon of the present invention does not include genes coding for the structural proteins of HCV (Core, E1, E2, and p7) to eliminate the transmitting property of the produced virus-like particle.

The above-mentioned elements may be derived from the same HCV strain or may be in the combined form (that is, chimera) derived from two or more different HCV strains. Preferred HCV strains include at least one strain selected from the group consisting of HCV strains of genotypes 1b and 2a, and the con1 strain, an HCV strain of genotype 1b, and the JFH1 strain, an HCV strain of genotype 2a, are more preferred. The HCV strain in the present invention may be an isolated strain resulting from natural or artificial mutation in the con1 strain or the JFH1 strain as a parent strain whose at least genotype is changed from that of the parent strain (derivative). At this time, the phenotypic trait may be the same as or different from that of the parent strain, but a strain having the same trait is preferred.

Examples of the HCV subgenomic RNA replicon include an HCV subgenomic RNA replicon having the 5' untranslated region, the sequence coding for the NS3, NS4A, NS4B, and NS5A proteins derived from HCV strain genomes other than the JFH1 strain (genotype 2a), the sequence coding for the NS5B protein of the JFH1 strain, and the 3' untranslated region; an HCV subgenomic RNA replicon having the 5' untranslated region, the sequence coding for the NS3, NS4A, NS4B, NS5A, and NS5B proteins, and the 3' untranslated region of the JFH1 strain; an HCV subgenomic RNA replicon having the 5' untranslated region, the sequence coding for NS3, NS4A, NS4B, NS5A, and NS5B proteins, and the 3' untranslated region of the HCV-con1 strain (genotype 1b, GenBank accession number AJ238799, Lohmann, V. et al., Science 285 (1999) p 110-113), and so forth. Furthermore, a desired foreign gene and an IRES sequence may be included between the 5' untranslated region and the sequence coding for the NS3 protein of these HCV subgenomic RNA replicons.

The 5' untranslated region, the sequence of structural proteins (Core, E1, E2, and p7), nonstructural proteins (NS2, NS3, NS4A, NS4B, NS5A, and NS5B), 3' untranslated region, and other sites on the HCV genomic RNA can be defined by using the full-length genomic cDNA sequence, for example, corresponding to the genomic RNA of the JFH 1 strain, an HCV strain of genotype 2a (JP Patent Publication (Kokai) No. 2002-171978 A) (GenBank accession number AB047639, Kato, T. et al., Gastroenterology, 125 (2003) p 1808-1817, SEQ ID NO: 10. The encoded amino acid sequence is also shown in SEQ ID NO: 11) as reference.

For example, in the full-length genome cDNA derived from the JFH1 strain, the 5' untranslated region that can be used as an element of the HCV subgenomic RNA replicon of the present invention is shown by nucleotide positions 1 to 340 of the nucleotide sequence of SEQ ID NO: 10, the region coding for from the Core protein to the p7 protein (Core, E1, E2, and p7) is shown by nucleotide positions 341 to 2779, and the region coding for from the NS3 protein to the 3' untranslated region (NS3, NS4A, NS4B, NS5A, NS5B, and 3'UTR) is shown by nucleotide numbers 3431 to 9678. Regions within genomic cDNA derived from other HCV strains can be identified by comparison with the sequences of these regions derived from the JFH1 strain.

An HCV subgenomic RNA replicon can be synthesized with a DNA-dependent RNA polymerase using a vector in which DNA complementary to the HCV subgenomic RNA is cloned into the downstream of a promoter for transcription of RNA from the DNA sequence. Examples of the promoter for transcription of RNA from a DNA sequence include T7, T3, SP6, and so forth, and the T7 promoter is preferred. An HCV subgenomic RNA can be synthesized by T7 polymerase. A cell in which an HCV subgenomic RNA replicon autonomously replicates can be prepared by introducing the thus synthesized HCV subgenomic RNA into a cell that allows propagation of HCV.

Preferred examples of the cell include animal cells such as, for example, vertebrate cells including cells of fish, reptiles, amphibians, birds, and mammals, and mammalian cells are most preferred. Further examples of the cell include normal cells derived from the liver, the uterine cervix, and the fetal kidneys, tumor cells, established cell lines thereof, and so forth. Examples thereof include cells such as Huh7, HepG2, IMY-N9, HeLa, and HEK293 (Date, T. et al., J. Biol. Chem., 279 (2004) p 22371-22376, Ito, T. et al., Hepatology 34 (2001) p 566-572), and Huh7, HepG2, and clones derived from these cells are preferred.

Examples of other methods for replicating the HCV subgenomic RNA in cultured cells include systems utilizing HCV cDNA without using an RNA replicon. When HCV cDNA is expressed using RNA polymerase II-type promoter, the CAP structure is added to the 5' end of the transcribed RNA, and the polyA chain is added to the 3' end. Therefore, the transcribed RNA is used as a template for protein synthesis on the ribosome and the replication of HCV genomic RNA does not occur. To solve this problem, Heller et al. prepared a DNA vector by ligating a ribozyme sequence to the 5' and 3' ends of the HCV genome and allowing the ribozyme to cleave the DNA transcribed by RNA polymerase II in a cell, so that HCV RNA to which CAP or polyA is not added can be synthesized in the cell (Heller T et al. Proc. Natl. Acad. Sci. USA., 102 (2005) p 2579-2583). A cell in which an HCV subgenomic RNA replicon replicates can be obtained by introducing this vector into a cell.

According to another method, a cell in which an HCV subgenomic RNA replicon replicates can be obtained by cloning DNA complementary to the HCV subgenomic RNA into a vector having an RNA polymerase I promoter/terminator system and introducing the vector into a cell that allows propagation of HCV. More specifically, pHH21 (Neumann G. et al., Proc. Natl. Acad. Sci. USA, 96 (1999) p 9345-9350) can be used. pHH21 is a vector comprising the human RNA polymerase I promoter as a promoter and the mouse RNA polymerase I terminator as a terminator. When the recognition sequence of the restriction enzyme BsmBI is added to the 5' and 3' ends of cDNA complementary to an HCV subgenomic replicon RNA by PCR, the cDNA is digested with BsmBI, the HCV genome is inserted into the BsmBI site of pHH21, and the HCV genome can be ligated without extra nucleotide sequences between the promoter/terminator and the HCV genome.

An HCV subgenomic RNA replicon or a vector such as a vector expressing the HCV subgenomic RNA replicon can be introduced into a cell using any techniques known to those skilled in the art. Examples of such introduction techniques include electroporation, particle gun, lipofection, calcium phosphate method, microinjection, DEAE dextran method, and so forth.

In the present invention, a cell in which the HCV subgenomic RNA replicon of the present invention replicates can be prepared according to the above descriptions. Since such an RNA replicon autonomously replicates continuously in the cell, a certain amount thereof is maintained even in a cell subject to RNA degradation. Therefore, the RNA replicon can be maintained in a cell into which the HCV subgenomic RNA replicon of the present invention, a vector expressing the HCV subgenomic RNA replicon, or the like is introduced as described above. In the present invention, "cell carrying an RNA replicon" means that the RNA replicon exists in the cell not transiently but continuously in a significant amount due to an autonomously replicating ability thereof.

According to the method of the present invention, a virus-like particle in which an HCV subgenomic RNA replicon is packaged can be produced by introducing a vector expressing the HCV structural proteins described below into a cell carrying the HCV subgenomic RNA replicon of the present invention.

3. Construction of HCV Structural Protein Expressing Vector

In the method of the present invention, it is preferable to express the HCV structural protein genes in a cell carrying an HCV subgenomic RNA replicon to supply the HCV structural proteins.

The HCV structural proteins consist of Core, E1, E2, and p7. The genes coding for these proteins to supply the HCV structural protein are not limited by HCV genotypes, and each of the genes may be derived from the same HCV strain or may be in the combined form (chimera) derived from two or more different HCV strains. It is sufficient that the HCV structural protein genes are derived from at least one virus strain selected from HCV strains of genotypes 1a, 1b, 2a, 2b, 3a, and 3b. Preferred HCV strains are at least one virus strain selected from the group consisting of 1a, 2a, 3a, and 3b, and more preferred HCV strains are at least one virus strain selected from the group consisting of HCV strains of genotype 1b and 2a. More preferred virus strains include those of at least one type selected from the group consisting of strains of genotype 1a such as H77c, 1, H, and HC-J1, strains of genotype 1b such as J1, con1, TH, J, JT, and BK, and strains of genotype 2a such as JFH1, HC-J6, JCH1, and J6CF. The H77 strain of genotype 1a, the J1 strain of genotype 1b, and the JFH1 strain of genotype 2a are more preferred. The JFH1 strain is most preferred (GenBank accession number AB047639, Kato, T. et al., Gastroenterology, 125 (2003) p 1808-1817).

The method for expressing these proteins may be any method so long as it is a method by which they can be expressed in a cell, preferably an animal cell, more preferably a mammalian cell. A method using an expression vector into which the above-mentioned genes are incorporated is preferred.

In the preferred method of the present invention, a vector expressing the HCV structural proteins (preferably, an expression vector including the HCV structural protein genes in a manner expressible under control of a promoter) is introduced into a cell carrying the HCV subgenomic RNA replicon described in the above section 2 and expressed to supply the HCV structural proteins.

Examples of the expression vector include CDM8, pEF1/Myc-His1,2,3, pEF4/Myc-His1,2,3, pcDNA3.1, pREP4, pCEP (all available from Invitrogen Corporation), pCI-neo (Promega Corporation), and so forth. pcDNA5/TO (Invitrogen Corporation), which includes a promoter whose expression can be regulated by tetracycline, can also be used. The promoter is not limited so long as it can express the genes in an animal cell, and examples thereof include the immediate early (IE) promoter of cytomegalovirus, early or late promoter of SV40, metallothionein promoter, retrovirus promoter, heat shock promoter, SRα promoter, elongation factor 1α promoter, albumin promoter, and so forth.

Furthermore, examples of available vectors include viral vectors. The viral vectors are not limited so long as they can infect an animal cell and express a desired foreign gene, and preferred examples thereof include retrovirus vector, adenovirus vector, Sindbis virus vector, and vaccinia virus vector. In particular, vaccinia virus vector is preferred since the vaccinia virus vector can express a large amount of gene product (Elroy-Stein, O., et al., Proc. Natl. Acad. Sci. USA, 86 (1989) p 6126-6130).

It is preferable that the HCV structural protein expressing vector used in the method of the present invention include the Core protein gene, E1 protein gene, E2 protein gene, and p7 protein gene as the HCV structural protein genes in a manner in which they can be expressed in the host cell. Examples of such an HCV structural protein expressing vector of the present invention include vectors including the Core protein gene, E1 protein gene, E2 protein gene, and p7 protein gene under control of a promoter that can express the inserted genes. In the present invention, the elongation factor 1α promoter carrying vector, into which the Core protein gene, E1 protein gene, E2 protein gene, and p7 protein gene are inserted under control of the elongation factor 1α (EF-1α) promoter, can be used as a particularly preferred HCV structural protein expressing vector. Here, the expression "elongation factor 1α promoter carrying vector" means a vector including the promoter sequence of the elongation factor 1α gene (EF-1α promoter: Mizushima et al., Nucleic Acids Res., 18 (1990) p 5322) located in a manner in which genes under control thereof can be expressed in the host cell. Examples thereof include pEF1/Myc-His1,2,3 and pEF4/Myc-His1,2,3 (both available from Invitrogen Corporation).

Another preferred example of the HCV structural protein expressing vector of the present invention is a vaccinia virus vector comprising the Core protein gene, E1 protein gene, E2 protein gene, and p7 protein gene in an expressible manner (recombinant vaccinia virus vector). Vaccinia virus strains such as, for example, the DIs, WR, and IBTd strains (Meis, R J & Condit, R C. Virol. 182 (1992) p 442-454) can be preferably used for preparation of a recombinant vaccinia virus vector. The method for preparing a recombinant vaccinia virus vector is also described in detail in the examples described later. In brief, a desired recombinant vaccinia virus vector can be produced by cloning the above-mentioned HCV structural protein genes under control of a vaccinia virus promoter such as p. 7.5 in a vaccinia virus transfer vector, further introducing the transfer vector into a cell infected by vaccinia virus by electroporation or the like, culturing the cell to produce viral particles, and further preferably selecting the virus and purifying it. Such a vaccinia virus vector can be prepared in the form of a recombinant virus-like particle.

Since the HCV structural proteins (Core, E1, E2, p7) and the nonstructural proteins (NS3, NS4A, NS4B, NS5A, and NS5B) are translated from the translated region as one polyprotein, subjected to limited digestion with protease, released, and produced, it is preferable to express these HCV structural proteins as a polyprotein of Core, E1, E2, and p7 in a continuous stretch, but these proteins may be expressed by separate expression vectors.

Whether the structural proteins are expressed in a cell into which a structural protein expressing vector is introduced can be detected by reacting a cell culture solution or proteins extracted from cells with antibodies against the structural proteins (WO2004/104198).

Specifically, for example, a protein sample extracted from cells is fractionated by SDS-polyacrylamide gel electrophoresis, blotted on a nitrocellulose membrane, and reacted with an anti-HCV protein antibody (e.g., anti-Core specific antibody or antiserum collected from a patient with hepatitis C), and the antibody can be detected (by western blotting).

Alternatively, cells expressing the HCV proteins are immunostained using a similar antibody, and expression and intracellular localization of these proteins can be confirmed.

4. Packaging of HCV Subgenomic RNA Replicon into Particle

In the method of the present invention, a virus-like particle in which an HCV subgenomic RNA replicon is packaged by the structural proteins is produced in a cell by supplying a vector expressing the HCV structural proteins into a cell carrying the HCV subgenomic RNA replicon.

To package in a viral particle an HCV subgenomic RNA replicon in a cell in which the HCV subgenomic RNA replicon replicates, a vector expressing the structural proteins (Core, E1, E2, and p7) can be introduced into the cell and expressed. Alternatively, the HCV subgenomic RNA can be introduced into a cell in which the structural proteins (Core, E1, E2, and p7) are stably expressed.

Examples of such an introduction method include known methods such as electroporation, particle gun, lipofection, calcium phosphate method, microinjection, and DEAE dextran method.

5. Production of Recombinant HCV Virus-Like Particle

The cell carrying an HCV subgenomic RNA replicon prepared as described above into which the HCV structural protein (Core, E1, E2, and p7) genes are introduced and expressed (recombinant HCV-like particle producing cell) can produce a recombinant virus-like particle. The produced recombinant HCV-like particle has an infecting ability and an ability of replicating the HCV subgenomic RNA. However, it does not have a transmitting property (transmitting ability), since the infected cell cannot produce a daughter viral particle.

Therefore, a recombinant HCV-like particle can be prepared in a cell culture system by culturing the recombinant HCV particle producing cell of the present invention. The HCV-like particle can be obtained preferably by culturing recombinant HCV-like particle producing cells and recovering a virus-like particle produced in the culture (preferably a culture solution). A virus-like particle can be recovered from the above-mentioned culture solution by techniques such as, for example, sucrose density gradient centrifugation.

The viral particle producing ability of the recombinant HCV-like particle producing cell of the present invention can be confirmed by any virus detection methods known to those skilled in the art. For example, the viral particle producing ability can be determined by fractionating a culture solution of cells that appear to produce a virus-like particle by a sucrose density gradient and measuring the density of each fraction and the concentration of the HCV Core protein or the HCV replicon RNA in the fraction to see whether specific gravity matches the known specific gravity of HCV. Furthermore, when the density of a fraction in which a peak of the Core protein is detected is lower than the density of the fraction obtained by fractionating the culture solution after treated with 0.25% NP40 (polyoxyethylene(9) octylphenyl ether), it can be determined that the cell has a virus-like particle producing ability.

Furthermore, whether a virus-like particle in a recombinant HCV-like particle producing cell has an infecting ability can be determined by detecting the phenotype of a foreign gene that exists in an HCV subgenomic RNA packaged in the viral particle. For example, if the foreign gene is a drug resistance gene, it can be assessed by inoculating the viral particle in an HCV-permissive cell, culturing usually for 2 to 3 weeks in the presence of this drug, and counting drug-resistant clones.

Furthermore, it can be confirmed that a virus-like particle in a recombinant HCV-like particle producing cell does not produce a daughter viral particle in an infected cell, by western blotting described above or the like whether the HCV structural proteins exist in an extract from the infected cell, preferably an infected cell culture supernatant sample.

A recombinant HCV-like viral particle produced by the method of the present invention has an ability of infecting a cell (preferably HCV-permissive cell). There is also provided a method for producing a recombinant hepatitis C virus infected cell comprising the steps of culturing a recombinant HCV-like particle producing cell and allowing a virus-like particle in the obtained culture (preferably culture broth) to infect another cell (preferably HCV-permissive cell). Here, the HCV-permissive cell is a cell having an ability of replicating HCV genomic RNA and/or being infected by HCV and is not limited to these examples. Specific examples of hepatic cells include primary hepatocyte, Huh7 cell, HepG2 cell, IMY-N9 cell, HeLa cell, and so forth. Specific examples of lymphoid cells include the Molt4 cell, HPB-Ma cell, Daudi cell, and so forth. However, hepatic and lymphoid cells are not limited to these examples.

Figure 1:
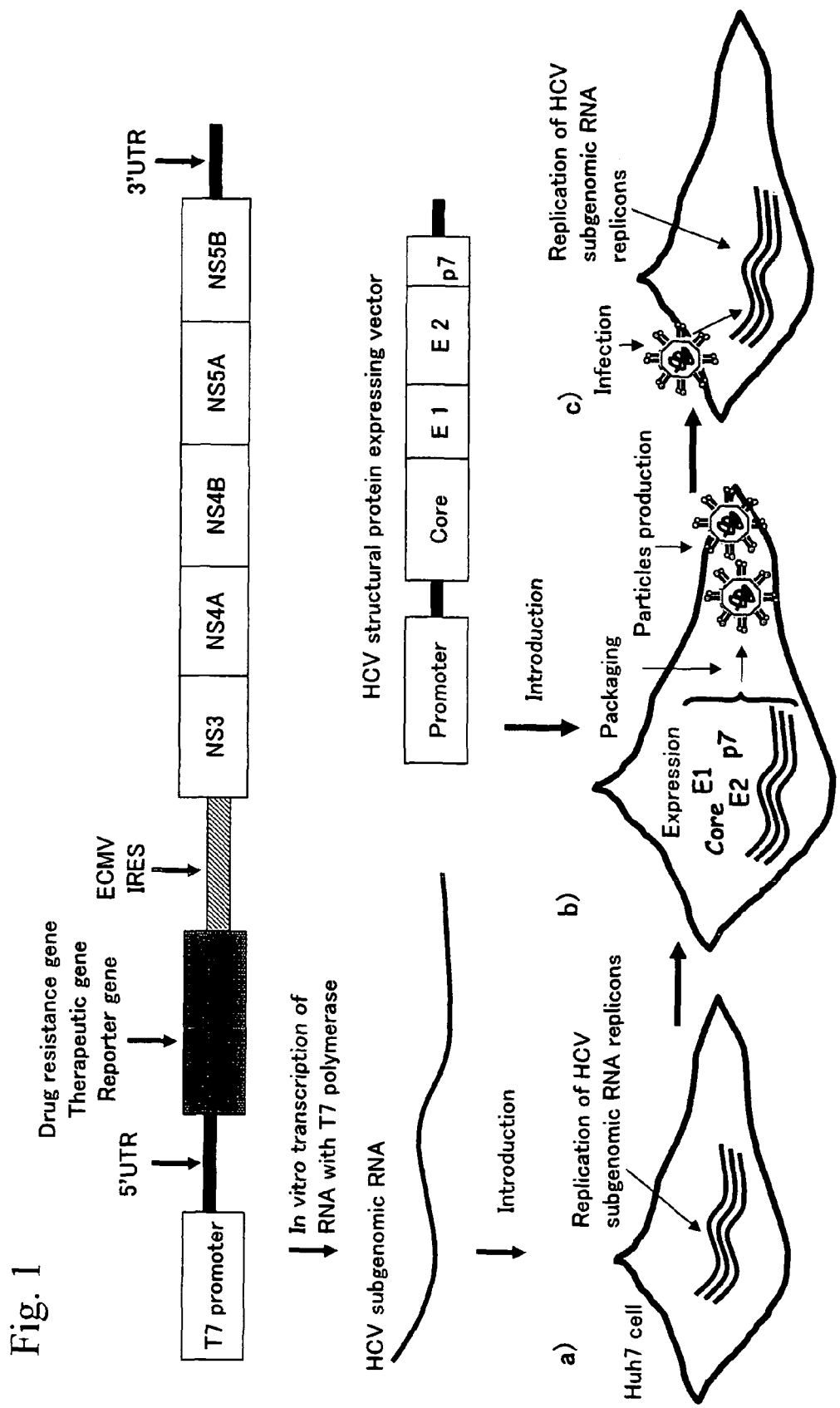

For easier understanding, the production processes of the recombinant HCV-like particle explained in the above sections 2 to 5 are schematically shown in FIG. 1.

6. Vector for Gene Introduction

The recombinant HCV-like particle of the present invention produced by the method of the present invention is characterized by having on the RNA genome a nucleotide sequence comprising the 5' untranslated region, the nucleotide sequence coding for the NS3, NS4A, NS4B, NS5A, and NS5B proteins, and the 3' untranslated region, derived from the above-mentioned HCV strains (at least one virus strain selected from genotypes 1a, 1b, 2a, 2b, 3a, and 3b, preferably 1b and 2a such as, for example, the con1 strain of genotype 1b and the JFH1 strain of genotype 2a).

In addition, the recombinant HCV-like particle of the present invention has an interesting characteristic that, when the HCV-like particle produced in a recombinant HCV-like particle producing cell by the method of the present invention is allowed to infect a cell (e.g., an HCV-permissive cell described above as an example), the above-mentioned HCV subgenomic RNA is replicated in the infected cell, but a daughter viral particle is not formed.

The recombinant HCV-like particle of the present invention can be used as a vector for gene introduction/expression by inserting a desired foreign gene into an HCV subgenomic RNA replicon packaged therein. Such a recombinant HCV-like viral particle of the present invention comprising a foreign gene can be prepared by preparing an HCV subgenomic RNA replicon in which the foreign gene is inserted between the 5' untranslated region and the IRES sequence and packaging it by the above-mentioned method of the present invention. Since the HCV particle produced in the recombinant HCV particle producing cell does not have a transmitting ability, it can also be used as a vector for gene introduction targeting hepatic or lymphoid cells or tissues.

Since an HCV subgenomic RNA packaged in a viral particle by the viral particle production method of the present invention is not incorporated into the chromosomal genome in an HCV-permissive cell infected by the virus-like particle of the present invention, it has an advantage that normal genes are not damaged or genes in the vicinity of the insertion site are not activated by the gene insertion.

Due to the above-mentioned characteristics, the vector of the present invention can be used for, for example, gene therapy or construction of transgenic animals by introducing a foreign gene.

Examples of the foreign gene (or foreign nucleic acid) to be introduced into an HCV subgenomic RNA replicon and packaged in a viral particle include, but not limited to, genes coding for proteins derived from mammals including humans, for example, various proteins involved in diseases such as proteins, polypeptides, or peptides including, for example, enzymes, cytokines, chemokines, hormones, antibodies, immunoregulatory molecules, tumor suppressing proteins, growth factors, membrane proteins, and vasoactive proteins; therapeutic nucleic acids such as antisense RNA and siRNA that inhibit or suppress translation of proteins, and so forth.

Target HCV-susceptible cells or tissues are mammal cells or tissues, preferably human cells or tissues such as, for example, human hepatic and lymphoid cells or tissues. The vector of the present invention is allowed to act on target cells or tissues under in vivo, in vitro, or ex vivo conditions. Preferably, the vector of the present invention can be used for treatment of humans, for example, gene therapy, treatment of cancer (e.g., liver cancer, lymphoma, etc.), and the like.

The contents of the specification and/or the drawings of JP Application No. 2005-287825, to which the present application claims the priority, are encompassed in the present specification.

All the publications, patents, and patent applications in their entireties that have been referred to in this application are hereby incorporated by reference into this application.

EXAMPLES

The present invention will be explained more specifically with reference to the following examples. However, these examples are only for illustration, and the scope of the present invention is not limited to these examples.

Example 1

Preparation of Replicon Carrying Cell

Plasmid DNA pSGR-JFH1 (middle diagram of FIG. 2) was constructed by replacing part of the structural regions and the nonstructural regions with the neomycin resistance gene (neo: also referred to as neomycin phosphotransferase gene) and EMCV-IRES (internal ribosome entry site of encephalomyocarditis virus) in pJFH1 which has been prepared by inserting DNA containing the full-length genome cDNA of the JFH-1 strain (genotype 2a), a hepatitis C virus strain isolated from a patient with fulminant hepatitis (JFH-1 clone: GenBank accession number AB047639) into the downstream of T7 promoter in the pUC19 plasmid. This construction procedure was performed according to a previous report (Lohmann et al., Science, 285 (1999) p 110-113).

Specifically, plasmid pJFH1 was digested with restriction enzymes AgeI and ClaI, and a sequence from pJFH1-derived 5'NTR to the Core region and the pRSV5NEO-derived neomycin resistance gene were ligated to the cleavage sites by PCR amplification, a fragment digested with the restriction enzymes AgeI and PmeI and a sequence from EMCV IRES to the NS3 region were ligated by PCR amplification, and a fragment digested with restriction enzymes PmeI and ClaI was inserted and ligated.

Subsequently, pSGR-JFH1 was digested with restriction enzyme XbaI. Then, 10 to 20 µg of these XbaI-digested fragments were further treated by incubation using 20 units of Mung Bean Nuclease (total volume of reaction mixture, 50 µl) at 30° C. for 30 minutes. Mung Bean Nuclease is an enzyme that catalyzes a reaction of selectively degrading a single-stranded portion in a double-stranded DNA. Usually, when RNA is synthesized using the above-mentioned XbaI-digested fragment as it is as a template, a replicon RNA is synthesized with extra four nucleotides of CTGA, which is a part of the recognition sequence of XbaI, added to the 3' end. Accordingly, in this example, by treating the XbaI-digested fragment with Mung Bean Nuclease, four nucleotides of CTGA were removed from the XbaI-digested fragment. Subsequently, to obtain a template DNA, a solution containing the XbaI-digested fragment treated with Mung Bean Nuclease was subjected to protein removal treatment according to a conventional method to purify the XbaI-digested fragment from which the four nucleotides of CTGA were removed.

Subsequently, RNA was synthesized in vitro by T7 RNA polymerase using this template DNA. For this RNA synthesis, the MEGAscript from Ambion was used. 20 µl of the reaction mixture containing 0.5 to 1.0 µg of template DNA was reacted according to the manufacturer's instructions.

After completion of RNA synthesis, DNase (2 units) was added to the reaction solution and reacted at 37° C. for 15 minutes, and then RNA extraction was further performed with acidic phenol to remove the template DNA.

0.01 ng to 10 µg of this RNA (replicon RNA) was mixed with total cellular RNA extracted from the Huh7 cell and adjusted so that the total RNA amount should be 10 µg. Then, the mixed RNA was introduced into the Huh7 cell by electroporation. The electroporated Huh7 cells were seeded on a culture dish and cultured for 16 to 24 hours, and then G418 (neomycin) was added to the culture dish at various concentrations. Then, the culture was continued while replacing the culture medium twice weekly. Colonies of viable cells were cloned from the culture dish after 21 days of the above-mentioned culture, and the culture was continued. Some strains of cell clones could be established by cloning such colonies. One cell strain carrying the HCV subgenomic RNA replicon was designated as 1H4.1.

Furthermore, the 5-15 cell, a cell strain carrying an HCV subgenomic RNA replicon (GenBank accession number, AJ242654; $I_{389}$/NS3-3'/wt in the lower column of FIG. 2) prepared from cDNA of the full-length genome derived from the Con-1 strain of HCV genotype 1b in the same manner as described above, that was prepared by introducing this RNA replicon into the Huh7 cell strain (Lohmann et al., Science, 285 (1999) p 110-113), was also used for experiments.

Example 2

Preparation of Structural Protein Expressing Vector

1) Structural Protein Expressing Plasmid Vector

A region including the structural region genes (nucleotide positions: 249 to 2781) of the JFH1 strain isolated from a patient with fulminant hepatitis (GenBank accession number AB047639) (Kato T. et al., J. Med. Viol. 64 (2001) p 334-339) was amplified by PCR. This DNA fragment was digested with NheI and EcoRI and thus an obtained fragment containing the structural genes was purified by agarose gel electrophoresis and blunt-ended by DNA polymerase. This blunt-ended cDNA was inserted into the downstream of the CAG promoter sequence (CAG) in a plasmid vector. Similarly, the above-mentioned cDNA containing the structural region genes obtained by digesting with NheI and EcoRI was inserted between the SpeI and EcoRI recognition sites in pEF4/Myc-His (Invitrogen Corporation), a vector carrying the elongation factor 1α gene promoter sequence (EF-1α (promoter: Mizushima et al., Nucleic Acids Res., 18 (1990) p 5322). The resulting obtained plasmids were designated as pCAGC-p7JFH1 and pEF4C-p7JFH1, respectively (FIG. 3).

2) Recombinant Vaccinia Virus Vector Expressing Structural Proteins

Figure 3:
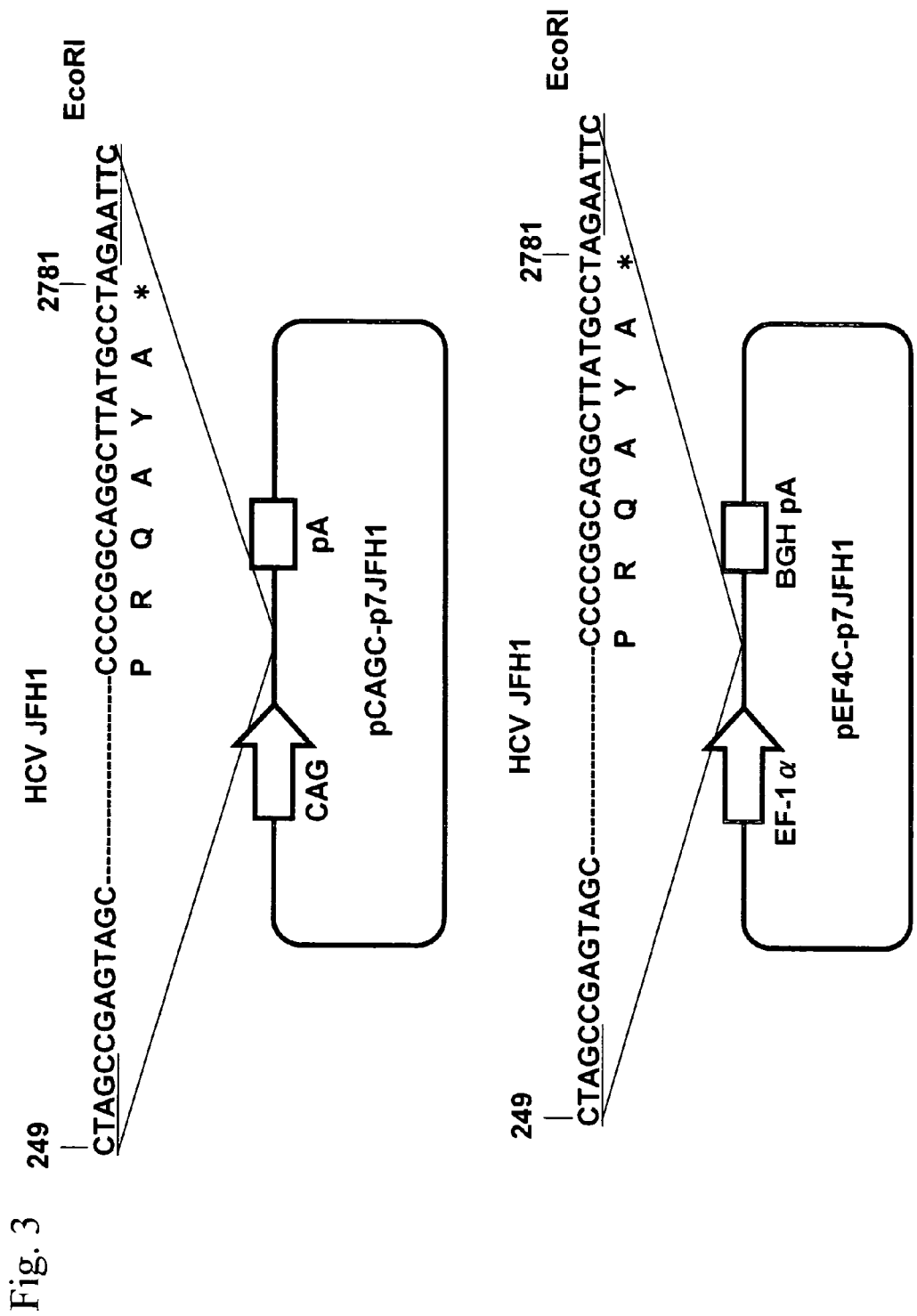
Figure 4:
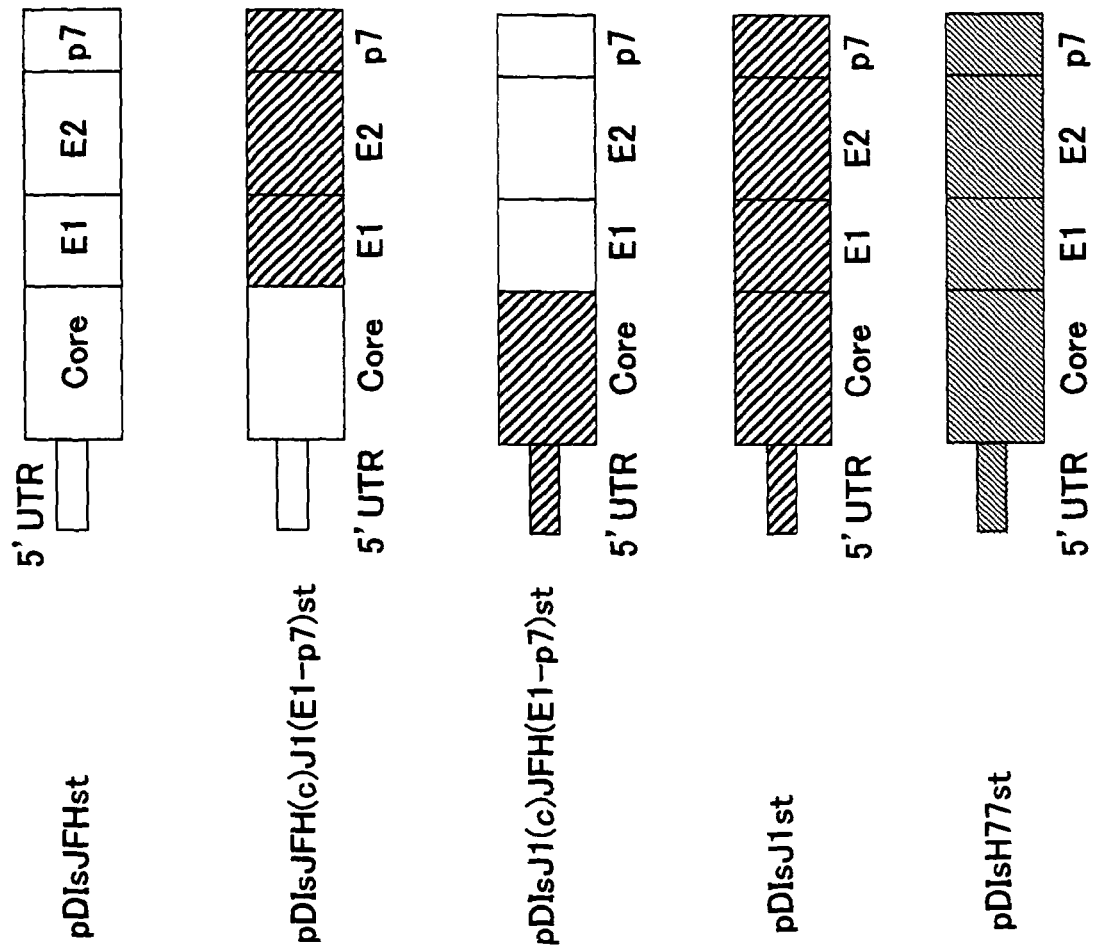
FIG. 4 shows maps of the HCV structural genes inserted into vectors pDIsHJFHst, pDIsH77st, pDIsJ1st, pDIsJ1(c)/JFH(E1-p7)st, and pDIsJFH(c)/J1(E1-p7)st. Differences in virus strains from which the vectors are derived are represented by shaded areas in the frame.
Figure 5:
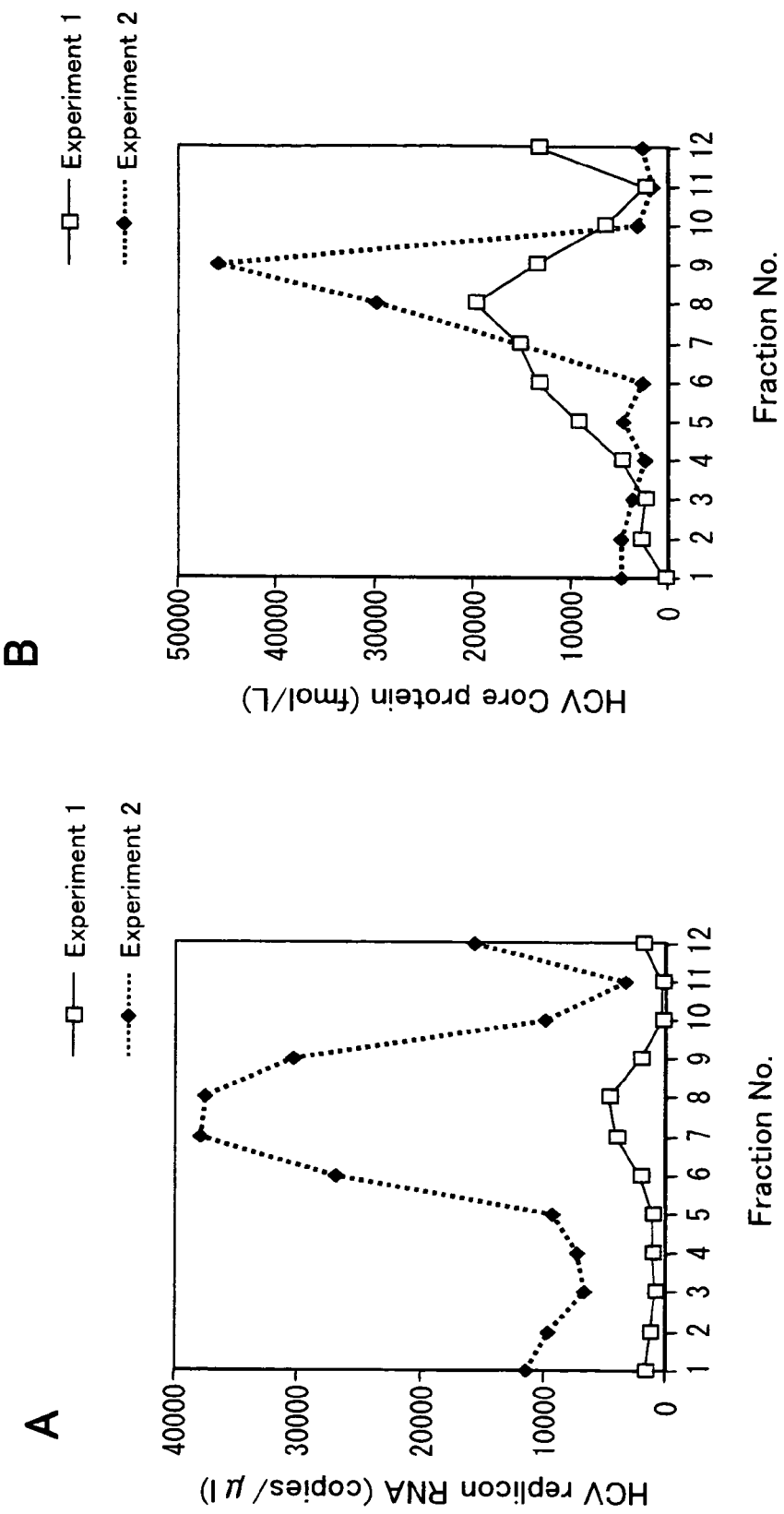
FIG. 5 shows graphs showing the amount of HCV replicon RNA (A) and the amount of the HCV Core protein (B) in each fraction obtained by introducing pEF4C-p7JFH1 into a replicon carrying cell strain IH4.1 and fractionating the cell culture supernatant (sup) by a sucrose density gradient. □, Experiment 1; ♦, Experiment 2.

To prepare a vector that contains the structural genes of the JFH1 strain and can express the proteins encoded by these genes, first, pEF4C-p7JFH1 shown in the upper diagram of FIG. 3 was digested with restriction enzymes BamHI and EcoRI, and the region coding for the Core, E1, E2, and p7 proteins was fractionated by agarose gel electrophoresis. Subsequently, this fragment was ligated to a vaccinia virus transfer vector pDIsgptmH5 which is designed so that the xanthine-guanine phosphoribosyl transferase (XGPRT) gene should be inserted together with a foreign gene of interest (Ohnishi, K. et al., Jap. J. Infect. Dis. 58 (2005) p 88-94; Ishii, K. et al., Virology 302 (2002) p 433-444). This pDIsgptmH5 is a transfer vector into which the XGPRT gene of *Escherichia coli* is incorporated under control of the vaccinia virus p7.5 promoter inserted into a cloning site of the pUc/DIs vector (Ishii, K. et al., Virology 302 (2002) p 433-444). The obtained vector was designated as pDIsJFHst.

A vector that comprises the structural genes of the H77c strain and can express the proteins encoded by these genes was prepared by the following method. First, a vector into which the HCV genomic cDNA of the H77c strain (GenBank accession number AF011751) was cloned as a template, 5 µl of 10× buffer accompanied by LA-PCR Kit (Takara Bio Inc.), 5 µl of 2.5 mM dNTP mixture, and 1 µl each of 10 µM H77/J1 forward primer (AAAGATCTGCGAAAGGCCTTGTGG-TACTGC: SEQ ID NO: 1) and H77 reverse primer (AA-GAGCTCTCATAACCCGACAAGAACAACGCCGCC: SEQ ID NO: 2) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and 68° C. for 5 minutes (per one cycle). When a part of the PCR products were subjected to electrophoresis on an agarose gel, about 2.5-kb amplification product was confirmed.

Accordingly, a ligation reaction was performed using 2 µl of the PCR products to ligate an amplification product into a plasmid vector. *Escherichia coli* was transformed with this ligation product according to a conventional method, and plasmid DNA was prepared using the obtained transformant. This plasmid DNA was digested with restriction enzymes that can remove the DNA fragment inserted into the plasmid DNA and subjected to agarose gel electrophoresis to confirm that about 2.5-kb DNA fragment was inserted into the plasmid DNA. The nucleotide sequence of the inserted DNA fragment was determined by a conventional method. As a result, the determined nucleotide sequence was found to match the sequence of nucleotide positions 271 to 2819 in the nucleotide sequence with GenBank accession number AF011751. Subsequently, this plasmid DNA was digested with BglII and SacI and subjected to agarose electrophoresis to isolate a DNA fragment containing the structural gene region of the H77c strain, which was ligated to the vaccinia virus transfer vector pDIsgptmH5 (Ohnishi, K. et al., Jap. J. Infect. Dis. 58 (2005) p 88-94; Ishii, K. et al., Virology 302 (2002) p 433-444). The vector obtained as a result was designated as pDIsH77st.

A vector that comprises the structural genes of the J1 strain and can express the proteins encoded by these genes was prepared by the following method. First, a vector into which the HCV genomic cDNA of the J1 strain (GenBank accession number D89815) was cloned as a template, 5 µl of 10× buffer accompanied by LA-PCR Kit (Takara Bio Inc.), 5 µl of 2.5 mM dNTP mixture, and 1 µl each of 10 µM H77/J1 forward primer (AAAGATCTGCGAAAGGCCTTGTGGTACTGC: SEQ ID NO: 1) and J1 reverse primer (AAGAGCTCTCATA-GACCTACAAAAACCCCGCCTCC: SEQ ID NO: 3) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and 68° C. for 5 minutes (per one cycle). When a part of the PCR products were subjected to electrophoresis on an agarose gel, about 2.5-kb amplification product was confirmed. Accordingly, a ligation reaction was performed using 2 µl of the PCR products to ligate an amplification product into the plasmid vector. *Escherichia coli* was transformed with this ligation product according to a conventional method, and plasmid DNA was prepared using the obtained transformant. This plasmid DNA was digested with restriction enzymes that can remove the DNA fragment inserted into the plasmid DNA and subjected to agarose gel electrophoresis to confirm that about 2.5-kb DNA fragment was inserted into the plasmid DNA. The nucleotide sequence of the inserted DNA fragment was determined by a conventional method. As a result, the determined nucleotide sequence was found to match the sequence of nucleotide positions 271 to 2819 in the nucleotide sequence with GenBank accession number D89815. Subsequently, this plasmid DNA was digested with BglII and SacI and subjected to agarose electrophoresis to isolate a DNA fragment containing the structural gene region of the J1 strain, which was ligated to the vaccinia virus transfer vector pDIsgptmH5 (Ohnishi, K. et al., Jap. J. Infect. Dis. 58 (2005) p 88-94; Ishii, K. et al., Virology 302 (2002) p 433-444). The resulting obtained vector was designated as pDIsJ1st.

A vector that comprises a chimeric structural gene sequence of the Core gene derived from the J1 strain and the E1, E2, and p7 genes derived from the JFH1 strain and can express the proteins encoded by these genes was prepared by the following method. First, to amplify the Core gene of the J1 strain, a vector into which the HCV genomic cDNA of the J1 strain (GenBank accession number D89815) was cloned as a template, 5 µl of 10× buffer accompanied by LA-PCR Kit (Takara Bio Inc.), 5 µl of 2.5 mM dNTP mixture, and 1 µl each of 10 µM H77/J1 forward primer (SEQ ID NO: 1) and J1/JFH1 reverse primer (GTAGCTGCTACTGGTATTCT-TCACCTGGGCAGCGGAAGCTGGGATGGTCAAACAG GACAG: SEQ ID NO: 4) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and 68° C. for 5 minutes (per one cycle). To amplify the E1, E2, and p7 genes of the JFH1 strain, a vector into which the HCV genomic cDNA of the JFH1 strain (GenBank accession number AB047639) was cloned as a template, 5 µl of 10× buffer accompanied by LA-PCR Kit (Takara Bio Inc.), 5 µl of 2.5 mM dNTP mixture, and 1 µl each of 10 µM J1/JFH1 forward primer (CTGTCCTGTTTGACCATCCCAGCTTC-CGCTGCCCAGGTGAAGAATACCAGTAGCA GCTAC: SEQ ID NO: 5) and JFH1 reverse primer (AAGAGCTCT-CAATCAATATCAACAAACCCACGCCT: SEQ ID NO: 6) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and at 68° C. for 5 minutes (per one cycle). The obtained amplified fragments were purified and dissolved in 50 µl of H₂O. 1 µl of each solution was diluted 100-fold, and 1 µl of each solution was combined into one mixture. Using this mixture as a template, 5 cycles of LA-PCR were performed under the above-mentioned conditions without adding primers. Then, H77 µl forward primer (SEQ ID NO: 1) and JFH1 reverse primer (SEQ ID NO: 6) were added, 10 cycles of LA-PCR were further performed, and the amplified chimeric DNA fragment was purified. This fragment was cloned into the plasmid vector, and the nucleotide sequence of the DNA fragment was determined. As a result, it was confirmed that the DNA fragment has a chimeric structural gene sequence of the Core gene derived from the J1 strain and the E1, E2, and p7 genes derived from the JFH1 strain. Subsequently, a fragment obtained by digesting this plasmid with BglII and SacI was ligated to the vaccinia virus transfer vector pDIsgptmH5 (Ohnishi, K. et al., Jap. J. Infect. Dis. 58 (2005) p 88-94; Ishii, K. et al., Virology 302 (2002) p 433-444). The resulting obtained vector was designated as pDIsJ1(c)/JFH1(E1-p7)st.

A vector that comprises a chimeric structural gene sequence of the Core gene derived from the JFH1 strain and the E1, E2, and p7 genes derived from the J1 strain and can express the proteins encoded by these genes was prepared by the following method. First, to amplify the Core gene of the JFH 1 strain, a vector into which the HCV genomic cDNA of the JFH1 strain (GenBank accession number AB047639) was cloned as a template, 5 µl of 10× buffer accompanied by LA-PCR Kit (Takara Bio Inc.), 5 µl of 2.5 mM dNTP mixture, and 1 µl each of 10 µM JFH1 forward primer (AAAGATCT-GCGAAAGGCCTTGTGGTACTGC: SEQ ID NO: 7) and JFH1/J1 reverse primer (GGTATATCCCGGACACGT-TGCGCACTTCATAAGCAGAGACCG-GAACGGTGATGC AGGAC: SEQ ID NO: 8) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and 68° C. for 5 minutes (per one cycle). To amplify the E1, E2, and p7 genes of the J1 strain, a vector into which the HCV genomic cDNA of the J1 strain (GenBank accession number D89815) was cloned as a template, 5 µl of 10× buffer accompanied by LA-PCR kit (Takara Bio Inc.), 5 µl of 2.5 mM dNTP mixture, and 1 µl each of 10 µM JFH1/J1 forward primer (GTCCTGCATCACCGTTCCG-GTCTCTGCTTATGAAGTGCGCAACGTGTCCGGGATA TACC: SEQ ID NO: 9) and 31 reverse primer (AA-GAGCTCTCATAGACCTACAAAAACCCCGCCTCC: SEQ ID NO: 3) were added, and deionized water was finally added to make 49 µl as a total volume. Then, 1 µl of Takara LA Taq (Takara Bio Inc.) was added, and PCR reaction was performed. The PCR reaction was performed under the following condition: 25 cycles of 98° C. for 20 seconds and 68° C. for 5 minutes (per one cycle). The obtained amplified fragments were purified and dissolved in 50 µl of H₂O. 1 µl of each solution was diluted 100-fold, and 1 µl of each solution was combined into one mixture. Using this mixture as a template, 5 cycles of LA-PCR were performed under the above-mentioned conditions without adding primers. Then, JFH1 forward primer (SEQ ID NO: 7) and J1 reverse primer (SEQ ID NO: 3) were added, 10 cycles of LA-PCR were further performed, and the amplified chimeric DNA fragment was purified. This fragment was cloned into the plasmid vector, and the nucleotide sequence of the DNA fragment was determined. As a result, it was confirmed that the DNA fragment has a chimeric structural gene sequence of the Core gene derived from the JFH1 strain and the E1, E2, and p7 genes derived from the J1 strain. Subsequently, a fragment obtained by digesting this plasmid with BglII and SacI was ligated to the vaccinia virus transfer vector pDIsgptmH5 (Ohnishi, K. et al., Jap. J. Infect. Dis. 58 (2005) p 88-94; Ishii, K. et al., Virology 302 (2002) p 433-444). The vector obtained as a result was designated as pDIsJFH(c)/J1(E1-p7)st.

The maps of the HCV structural gene sequences (chimeric structural gene sequence) inserted into the vectors prepared as described above, pDIsJFHst, pDIsH77st, pDIsJ1st, pDIsJ1(c)/JFH(E1-p7)st, and pDIsJFH(c)/J1(E1-p7)st, are shown in FIG. 4.

The recombinant vaccinia virus vector DIs strain carrying each of the above-mentioned vectors was prepared and selected as follows, for example.

500 μl of virus solution containing about $10^6$ plaque forming units (pfu) of the vaccinia virus DIs strain was inoculated on an 80-mm plate on which about $10^7$ chick embryo fibroblast (CEF) cells were seeded, and the virus was allowed to infect cells by shaking every 15 minutes 8 times. Then, Dulbecco's Modified Eagle Medium (DMEM) with 1 ml of 10% fetal calf serum (FCS) was added, and the mixture was cultured at 37° C. under 5% $CO_2$ for 2 hours. The medium was removed, cells were washed with phosphate-buffered serine (PBS), and 0.5 ml of 0.05% trypsin solution was added to release the cells. Then, the cell suspension was centrifuged at 2000 rpm for 3 minutes to recover the cells, and the cells were suspended in 400 μl of PBS. 10 μg of the above-mentioned transfer vector was dissolved in this cell suspension, and electroporation was performed in a 0.4-cm cuvette using Gene Pulser II (Bio-Rad Laboratories, Inc.), with a voltage applied once at 250 v and 500 μFD. The cells were suspended in 2 ml of DMEM containing 10% FCS, seeded on a 35-mm plate, and cultured at 37° C. under 5% $CO_2$ for 7 days. The infected cells were recovered with the medium, lyophilized 3 times, ultrasonicated for 2 minutes, and then diluted 10-, 100-, or 1000-fold with the same medium. $10^6$ cells were seeded on a 35-mm plate, followed by addition of 25 μg/ml of MPA, 250 μg/ml of xanthine, and 15 μg/ml of hypoxanthine to the medium (DMEM containing 10% FCS), and cultured overnight. Then, the above-mentioned diluted cell solutions were inoculated. The virus was allowed to infect cells by shaking every 15 minutes 8 times, the diluted cell solution was removed, then 2 ml of 1% soft-agar added medium (DMEM with 10% FCS; which contains MPA, xanthine, and hypoxanthine) was added, and the mixture was solidified and cultured at 37° C. under 5% $CO_2$ for 7 days. The formed plaque portions were picked up with a Pasteur pipette, suspended in 200 μl of DMEM containing 10% FCS, and ultrasonicated for 2 minutes to release the virus from agar. This culture solution was diluted 10-, 100-, and 1000-fold with the same medium, the same plaque assay procedure as described above was repeated further twice to purify the recombinant virus, and the processes were scaled up by infecting the CEF cells.

Viral vectors (recombinant virus-like particles) prepared as described above from pDIsJFHst, pDIsH77st, pDIsJ1st, pDIsJ1(c)/JFH(E1-p7)st, and pDIsJFH(c)/J1(E1-p7)st were designated as DIsJFHst, DIsH77st, DIsJ1st, DIsJ1(c)/JFH(E1-p7)st, and DIsJFH(c)/J1(E1-p7)st, respectively.

Example 3

Introduction of Structural Protein Expressing Vector into Replicon Carrying Cell and Production of Structural Protein To express the HCV structural proteins in a replicon carrying cell, the HCV structural protein expressing vector pCAGC-p7JFH1 or pEF4C-p7JFH1 prepared in Example 2 was introduced into a replicon carrying cell by lipofection and the like. Furthermore, the viral vectors expressing the HCV structural proteins prepared in Example 2, DIsJFHst, DIsH77st, DIsJ1st, DIsJ1(c)/JFH(E1-p7)st, and DIsJFH(c)/J1(E1-p7)st, were allowed to infect replicon carrying cells.

1) Introduction of Structural Protein Expressing Plasmid Vector pCAGC-p7JFH1 was introduced into the replicon carrying cell 5-15 by lipofection, then the cells were continuously cultured in an 8 ml culture solution, and the culture supernatant was recovered at 4 days to quantify the HCV Core protein. However, the amount was below detection limit.

Meanwhile, pEF4C-p7JFH1 was introduced into the replicon carrying cell IH4.1 by lipofection. As a result, the HCV Core protein could be detected in the culture supernatant by western blotting. Accordingly, the replicon carrying cells IH4.1 into which pEF4C-p7JFH1 was introduced were cultured for 4 days, and then a culture medium (8 ml) was collected and centrifuged at 8,000 g and 4° C. for 60 minutes to collect the culture supernatant. Subsequently, this supernatant was centrifuged using SW20 Rotor (Beckman) at 25,000 rpm and 4° C. for 4 hours, and pellets were suspended in 1 ml of buffer. The sample was overlaid on 10 to 60% sucrose density gradients prepared in a tube for SW41E Rotor (Beckman) and centrifuged at 35,000 rpm and 4° C. rpm for 16 hours. The 10 to 60% sucrose density gradients were prepared by layering 2 ml of 60% (weight/weight) sucrose solution (dissolved in 50 mM Tris, pH 7.5/0.1 M NaCl/1 mM EDTA), 1 ml of 50% sucrose solution, 1 ml of 40% sucrose solution, 1 ml of 30% sucrose solution, 1 ml of 20% sucrose solution, and 1 ml of 10% sucrose solution in a centrifuge tube.

After completion of centrifugation, 0.5 ml each of fractions was collected from the bottom of the tube. The density, the HCV Core protein concentration, and the RNA concentration were determined for each fraction. The HCV Core protein was quantified by ortho-HCV antigen IRMA test (Aoyagi et al., J. Clin. Microbiol., 37 (1999) p 1802-1808). HCV replicon RNA was quantified according to the method by Takeuchi (Takeuchi et al., Gastroenterology, 116 (1999) p 636-642). As shown in FIG. 5, the peaks of the replicon RNA and the Core protein matched and were both in fraction 8 in two experiments. The density of this fraction matched the reported density of the HCV particle, with about 1.17 g/ml. This suggested that viral particles were produced.

2) Introduction of HCV Structural Protein Expressing Recombinant Vaccinia Virus Vector $2\times10^6$ cells of the replicon carrying cell strain 5-15 were seeded on a 10-cm dish, and 0.5 pfu/cell of DIsJFHst was allowed to infect the replicon carrying cell strain on the following day. The culture was continued in an 8 ml culture medium. After 4 days of culture, the culture solution was recovered and centrifuged at 8,000 g and 4° C. for 60 minutes, and the culture supernatant was collected. Then, this supernatant was centrifuged using SW20 Rotor (Beckman) at 25,000 rpm and 4° C. for 4 hours, pellets equivalent to 8 ml of the cell culture solution were suspended in 1 ml of buffer with or without 0.2% NP40. The sample was incubated at 4° C. for 20 minutes, overlaid on 10 to 60% sucrose density gradients in a tube for SW41E Rotor (Beckman), and centrifuged at 35,000 rpm and 4° C. for 16 hours. The 10 to 60% sucrose density gradient were prepared by layering 2 ml of 60% (weight/weight) sucrose solution (dissolved in 50 mM Tris, pH 7.5/0.1 M NaCl/1 mM EDTA), 1 ml of 50% sucrose solution, 1 ml of 40% sucrose solution, 1 ml of 30% sucrose solution, 1 ml of 20% sucrose solution, and 1 ml of 10% sucrose solution in a centrifuge tube.

After completion of centrifugation, 0.5 ml each of fractions was recovered from the bottom of the tube. The density and the HCV Core protein concentration were determined for each fraction. The HCV Core protein was quantified by ortho-HCV antigen IRMA test (Aoyagi et al., J. Clin. Microbiol., 37 (1999) p 1802-1808).

Results of two independent experiments are shown in FIG. 6. In the NP40 untreated group (treated with PBS), the density of the particle containing the Core protein was 1.16 g/ml (fraction 7). In the NP40 treated group, the density of the particle containing the Core protein was 1.21 g/ml (fraction 9). This suggested that a surface membrane that had a light specific gravity because of lipids contained was removed from the viral particle by NP40, forming a core particle having the nucleic acid and the Core protein alone without a virus-like structure, and thus the specific gravity increased. This suggested that a complete viral particle was produced in this experimental system.

In the same manner as described above, viral vectors DIsJ1st, DIsJ1(c)/JFH(E1-p7)st, and DIsJFH(c)/J1(E1-p7)st were further allowed to infect the replicon carrying cell strain 5-15. 8 ml of supernatant obtained by culturing the cells for 4 days after infection was concentrated with an ultrafiltration membrane and fractionated by the above-mentioned sucrose density gradient centrifugation. The density and the HCV Core protein concentration were determined for each fraction. The density distribution pattern of the HCV Core protein showed that the produced virus-like particle was contained in the culture supernatant of cells infected by DIsJ1st, DIsJ1(c)/JFH(E1-p7)st, or DIsJFH(c)/J1(E1-p7)st.

Example 4

Confirmation of Infecting Ability of Recombinant HCV-like Particle

As shown in FIG. 1, the recombinant HCV particle prepared in the above-described examples has the neo gene as a drug resistance marker. Therefore, to confirm that the particle obtained in the Example 3 has an infecting ability, it is sufficient to allow this particle to infect the Huh7 cell and examine whether G418 (neomycin) resistance colonies can be obtained.

DIsJFHst was allowed to infect the replicon carrying cell strain 5-15, the culture supernatant obtained by culturing the cells for 4 days was concentrated 30 times by ultrafiltration membrane (cut off, $1\times10^5$ Da) to infect the Huh7 cells. After infection, 1 mg/ml G418 was added to the culture dish. Then, the culture was continued while replacing the culture medium twice weekly. After cultured for 21 days after seeding, viable cells were stained with crystal violet. As a result, colony formation was confirmed.

If the HCV structural proteins are not detected in an infected cell, it means that daughter particles are not produced in the infected cell. Therefore, colonies formed in this experiment were propagated, and cell extracts thereof were prepared. Then, proteins in these extracts were analyzed by SDS-PAGE and western blotting. In the analyses, the Huh7 cell was transiently transfected by the expression plasmid DNA including the Core gene, and the obtained cell extract was used as a positive control. Furthermore, a cell extract obtained from the Huh7 cell that was not transfected was used as a negative control. A sample extracted from each cell clone was subjected to SDS-PAGE and then blotted on a PVDF membrane (Immobilon-P, Millipore), and the Core protein translated in the cell was analyzed by ECL (Amersham Pharmacia Biotech Pharmacia) using an anti-Core specific antibody (clone 2H9 antibody) and an HRP-labeled secondary antibody that recognizes the antibody. As a result, the Core protein was not detected in the infected cells. Therefore, it was determined that no daughter viral particle was produced in the infected cells. This means that, after the recombinant HCV-like particle produced by the method of the present invention once infects another cell, it is not further reproduced as a particle, thus not having an ability of further spreading infection to other cells (transmitting ability).

INDUSTRIAL APPLICABILITY

A recombinant HCV-like particle having an infecting property but not a transmitting property in which an HCV subgenomic RNA containing a desired foreign gene is packaged, and a method for producing the same can be provided by the present invention. Since such a recombinant HCV-like particle having an infecting property has an advantage of lacking a transmitting property, it can be used in gene therapy via in vivo or ex vivo gene introduction into hepatic or lymphoid cells or tissues of mammals, in particular, humans, or can be used as a viral vector for constructing a transgenic animal or as an attenuated vaccine.

SEQUENCE LISTING FREE TEXT

The sequences of SEQ ID NOS: 1 to 9 represent primers.

The invention claimed is:

1. A method for producing a recombinant hepatitis C virus-like particle comprising, introducing into
   (i) a cell carrying a subgenomic RNA replicon comprising a nucleotide sequence comprising the 5' untranslated region, the nucleotide sequence coding for the NS3, NS4A, NS4B, NS5A, and NS5B proteins, and the 3' untranslated region of a genome RNA derived from hepatitis C virus strain of genotype 1b which is a con1 strain or a strain derived therefrom,
   (ii) a vaccinia virus vector or an EF-1α promoter carrying vector expressing the Core, E1, E2, and p7 proteins derived from at least one virus strain selected from the group consisting of hepatitis C virus strains of genotype 1a, 1b, 2a, 2b, 3a, and 3b that is different from the hepatitis C virus strain as defined in the (i),
   culturing the cell, and recovering the produced virus-like particle.

2. The method according to claim 1, wherein the hepatitis C virus strain of genotype 1a as defined in the (ii) is the H77c, 1, H, or HC-J1 strain.

3. The method according to claim 1, wherein the hepatitis C virus strain of genotype 1b as defined in the (ii) is the J1, TH, J, JT, or BK strain.

4. The method according to claim 1, wherein the hepatitis C virus strain of genotype 2a as defined in the (ii) is the JFH1, HC-J6, JCH1, or J6CF strain.

5. The method according to claim 1, wherein the hepatitis C virus strain of genotype 3a as defined in the (ii) is the NZL1, K3a/650, 452, or E-b1 strain.

6. The method according to claim 1, wherein the hepatitis C virus strain of genotype 3b as defined in the (ii) is the Tr strain.

7. The method according to claim 1, wherein the RNA replicon further comprises at least one internal ribosome entry site (IRES) sequence and/or at least one foreign gene.

8. The method according to claim 1, wherein the IRES sequence and/or the foreign gene is positioned between the 5' untranslated region and the sequence coding for the NS3 protein.

9. The method according to claim 1, wherein the cell is an animal cell.

10. The method according to claim 9, wherein the animal cell is the Huh7 cell, the HepG2 cell, or an established cell line derived from these cells.

* * * * *